United States Patent [19]

Takematsu et al.

[11] Patent Number: 4,657,581
[45] Date of Patent: Apr. 14, 1987

[54] HERBICIDAL AMIDE COMPOUNDS AND THEIR USES

[75] Inventors: Tetsuo Takematsu; Yasutomo Takeuchi, both of Utsunomiya; Kozo Hiraishi, Nagaokakyo; Toshikazu Fujii, Neyagawa; Shoji Nishimula, Joyo; Motoyuki Suzuki, Shiga; Masahiro Sato, Kyoto; Hiroshi Hayashi, Otsu, all of Japan

[73] Assignee: Sanyo Chemical Industries, Ltd., Kyoto, Japan

[21] Appl. No.: 733,244

[22] Filed: May 13, 1985

[30] Foreign Application Priority Data

May 18, 1984 [JP] Japan ................... 59-100898
Aug. 30, 1984 [JP] Japan ................... 59-181683
Sep. 27, 1984 [JP] Japan ................... 59-203190
Sep. 27, 1984 [JP] Japan ................... 59-203191

[51] Int. Cl.$^4$ .............. A01N 37/38; A01N 37/18; C07C 103/76; C07C 103/737
[52] U.S. Cl. ............... 71/118; 564/172; 564/173; 564/180
[58] Field of Search ............ 564/180, 172, 173; 71/118

[56] References Cited

U.S. PATENT DOCUMENTS 2,040,397  5/1936  Morschel ................. 564/173
3,362,992  1/1968  Schwartz ................. 71/118
4,484,942  11/1984 Kirino et al. ............. 71/118

FOREIGN PATENT DOCUMENTS 0058658  4/1982  Japan ................... 564/180

OTHER PUBLICATIONS

Pracejus et al., *J. Org. Chem.* 46(12), 1981, pp. 2547–2557.
Sidgwick, *The Organic Chemistry of Nitrogen*, pp. 95 and 225 (1966).

*Primary Examiner*—Charles F. Warren
*Assistant Examiner*—C. S. Greason
*Attorney, Agent, or Firm*—Oblon, Fisher, Spivak, McClelland & Maier

[57] ABSTRACT

An amide compound of formula 1:

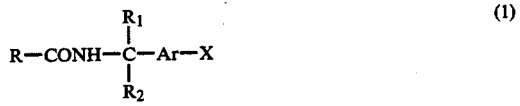

wherein R is 1,2,3,4-tetrahydro-1-naphthyl, 1,4-dihydro-1-naphthyl or 3,4-dihydro-1-naphthyl; $R_1$ is hydrogen or methyl; $R_2$ is hydrogen or an alkyl; Ar is a phenylene group; and X is hydrogen, a halogen, methyl or methoxy. This amide is useful as a herbicide.

13 Claims, No Drawings

HERBICIDAL AMIDE COMPOUNDS AND THEIR USES

BACKGROUND OF THE INVENTION

1. Field of the Invention

The present invention relates to amide compounds of di- or tetrahydro-1-naphthoic acid, to a process for producing the same, to a precursor thereof and to herbicidal compositions containing the same.

2. Discussion of the Background

In the past, amide compounds such as phenylacetoamide compounds have exhibited utility as amide-type herbicides.

SUMMARY OF THE INVENTION

Accordingly, one object of the present invention is to provide an amide compound which exhibits improved herbicidal activity.

Another object of the invention is to provide an amide-type herbicide which exhibits a substantially reduced phytotoxicity to essentially no phytotoxicity at all.

Still another object of the invention is to provide a process for economically producing a herbicidal amide compound and a precursor therefor.

Yet another object of the invention is to provide a herbicidal composition which exhibits improved selectivity.

Briefly, these and other objects of the present invention as hereinafter will become more readily apparent can be attained by an amide compound of the formula:

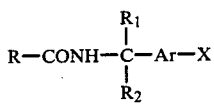

wherein R is 1,2,3,4-tetrahydro-1-naphthyl, 1,4-dihydro-1-naphthyl or 3,4-dihydro-1-naphthyl; $R_1$ is hydrogen or methyl; $R_2$ is hydrogen or alkyl; Ar is phenylene; and X is hydrogen, halogen, methyl or methoxy.

DETAILED DESCRIPTION OF THE PREFERRED EMBODIMENTS

The compounds of the present invention can be classified into groups of compounds of formulae (1a), (1b) and (1c).

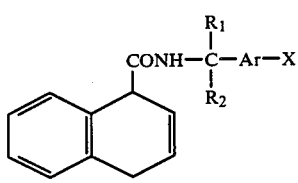

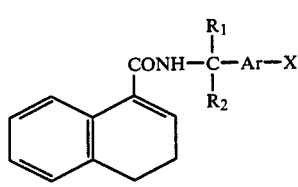

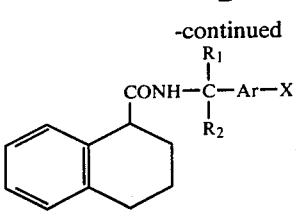

Specific examples of compounds of the invention and the analytical results obtained from these compounds are listed in Tables 1-5. In Tables 1-3, Me represents methyl, Et represents ethyl, i-Pr represents iso-propyl, and the numerical values in parentheses represent theoretical values.

TABLE 1

Compounds of the formula (1a)

| No. | $R_1$ | $R_2$ | X | Melting point, °C. | C, % | H, % | N, % |
|---|---|---|---|---|---|---|---|
| I-1 | H | H | H | 146.0–147.0 | 82.22 (82.10) | 6.39 (6.51) | 5.29 (5.32) |
| I-2 | H | H | 2-Cl | 133.0–134.0 | 72.39 (72.60) | 5.55 (5.42) | 4.68 (4.68) |
| I-3 | H | H | 3-Cl | 122.5–123.0 | 72.37 (72.60) | 5.41 (5.42) | 4.73 (4.70) |
| I-4 | H | H | 4-Cl | 146.0–147.0 | 72.71 (72.60) | 5.38 (5.42) | 4.71 (4.70) |
| I-5 | H | Me | H | 171.0–172.0 | 82.11 (82.28) | 6.99 (6.90) | 5.10 (5.05) |
| I-6 | H | Me | 2-Me | 126.0–172.0 | 82.60 (82.44) | 7.32 (7.26) | 4.78 (4.81) |
| I-7 | H | Me | 2-OMe | 147.5–148.0 | 78.30 (78.14) | 6.92 (6.89) | 4.60 (4.56) |
| I-8 | H | n-Pr | H | 148.5–150.0 | 82.43 (82.59) | 7.63 (7.59) | 4.51 (4.59) |
| I-9 | H | i-Pr | H | 147.0–148.0 | 82.45 (82.59) | 7.64 (7.59) | 4.61 (4.59) |
| I-10 | H | i-Pr | 4-Cl | 162.5–163.5 | 74.20 (74.22) | 6.48 (6.52) | 4.09 (4.12) |
| I-11 | Me | Me | H | 162.0–163.0 | 82.39 (82.44) | 7.31 (7.26) | 4.87 (4.81) |
| I-12 | Me | Me | 2-F | 153.0–154.0 | 77.54 (77.64) | 6.47 (6.52) | 4.49 (4.53) |
| I-13 | Me | Me | 4-F | 165.0–166.5 | 77.71 (77.64) | 6.59 (6.52) | 4.48 (4.53) |
| I-14 | Me | Me | 2-Cl | 116.5–118.5 | 73.65 (73.72) | 6.22 (6.19) | 4.28 (4.30) |
| I-15 | Me | Me | 3-Cl | 173.0–174.5 | 73.81 (73.72) | 6.25 (6.19) | 4.33 (4.30) |
| I-16 | Me | Me | 4-Cl | 184.0–185.5 | 73.66 (73.72) | 6.11 (6.19) | 4.34 (4.30) |
| I-17 | Me | Me | 4-Br | 180.5–182.0 | 64.71 (64.87) | 5.49 (5.44) | 3.80 (3.78) |
| I-18 | Me | Me | 2-Me | 110.5–112.0 | 82.50 (82.59) | 7.62 (7.59) | 4.62 (4.59) |
| I-19 | Me | Me | 3-Me | 158.5–159.5 | 82.70 (82.59) | 7.53 (7.59) | 4.58 (4.59) |
| I-20 | Me | Me | 4-Me | 170.0–171.0 | 82.72 (82.59) | 7.64 (7.59) | 4.50 (4.59) |
| I-21 | Me | Me | 3-OMe | 120.0–121.0 | 78.53 (78.47) | 7.18 (7.21) | 4.33 (4.33) |
| I-22 | Me | Me | 4-OMe | 140.0–141.0 | 78.31 (78.47) | 7.15 (7.21) | 4.32 (4.36) |
| I-23 | Me | Et | H | 133.5–135.0 | 82.39 (82.59) | 7.64 (7.59) | 4.40 (4.59) |
| I-24 | Me | Et | 4-Cl | 183.0–184.5 | 74.21 (74.22) | 6.43 (6.52) | 4.06 (4.12) |

TABLE 2

Compounds of the formula (1b)

| No. | $R_1$ | $R_2$ | X | Melting point, °C. | C, % | H, % | N, % |
|---|---|---|---|---|---|---|---|
| II-1 | H | H | H | 121.5–122.5 | 82.00 (82.10) | 6.47 (6.51) | 5.36 (5.32) |

TABLE 2-continued

Compounds of the formula (1b)

| No. | R₁ | R₂ | X | Melting point, °C. | C, % | H, % | N, % |
|---|---|---|---|---|---|---|---|
| II-2 | H | H | 3-Cl | 175.0–176.5 | 72.55 (72.60) | 5.38 (5.42) | 4.65 (4.70) |
| II-3 | H | H | 4-Cl | 144.0–145.0 | 82.19 (82.28) | 6.86 (6.90) | 5.01 (5.05) |
| II-4 | H | Me | 2-Me | 136.5–138.0 | 82.53 (82.44) | 7.25 (7.26) | 4.77 (4.81) |
| II-5 | H | Me | 2-OMe | 155.5–157.0 | 78.15 (78.15) | 6.82 (6.89) | 4.53 (4.56) |
| II-6 | H | n-Pr | H | 138.0–139.0 | 82.60 (82.59) | 7.63 (7.59) | 4.61 (4.59) |
| II-7 | H | i-Pr | H | 167.0–168.0 | 82.66 (82.59) | 7.51 (7.59) | 4.57 (4.59) |
| II-8 | H | i-Pr | 4-Cl | 173.5–174.0 | 74.27 (74.22) | 6.56 (6.52) | 4.17 (4.12) |
| II-9 | Me | Me | H | 157.0–158.0 | 82.36 (82.44) | 7.31 (7.26) | 4.81 (4.81) |
| II-10 | Me | Me | 2-F | 140.5–141.5 | 77.56 (77.64) | 6.57 (6.52) | 4.50 (4.53) |
| II-11 | Me | Me | 4-F | 162.5–163.5 | 77.59 (77.64) | 6.51 (6.52) | 4.59 (4.53) |
| II-12 | Me | Me | 2-Cl | 137.0–138.0 | 73.81 (73.72) | 6.22 (6.19) | 4.26 (4.30) |
| II-13 | Me | Me | 3-Cl | 147.5–149.0 | 73.79 (73.72) | 6.20 (6.19) | 4.25 (4.30) |
| II-14 | Me | Me | 4-Cl | 149.5–151.0 | 73.66 (73.72) | 6.24 (6.19) | 4.31 (4.30) |
| II-15 | Me | Me | 4-Br | 162.5–163.5 | 64.81 (64.87) | 5.50 (5.44) | 3.80 (3.78) |
| II-16 | Me | Me | 2-Me | 165.0–166.0 | 82.50 (82.59) | 7.62 (7.59) | 4.62 (4.59) |
| II-17 | Me | Me | 3-OMe | 97.0–98.5 | 78.37 (78.47) | 7.18 (7.21) | 4.41 (4.36) |
| II-18 | Me | Me | 4-OMe | 110.5–111.5 | 78.49 (78.47) | 7.16 (7.21) | 4.33 (4.36) |

TABLE 3

Compounds of the formula (1c)

| No. | R₁ | R₂ | X | Melting point, °C. | C, % | H, % | N, % |
|---|---|---|---|---|---|---|---|
| III-1 | H | H | H | 121.5–122.5 | 81.47 (81.48) | 7.15 (7.22) | 5.34 (5.28) |
| III-2 | H | H | 2-Cl | 157.0–158.5 | 72.03 (72.11) | 5.99 (6.05) | 4.70 (4.67) |
| III-3 | H | H | 4-Cl | 121.5–122.0 | 81.55 (81.68) | 7.64 (7.58) | 5.08 (5.01) |
| III-4 | H | Me | 2-Me | 193.0–194.5 | 81.93 (81.87) | 7.90 (7.90) | 4.82 (4.77) |
| III-5 | H | Me | 2-OMe | 162.0–163.5 | 77.51 (77.64) | 7.39 (7.49) | 4.47 (4.53) |
| III-6 | H | n-Pr | H | 144.5–145.5 | 81.79 (81.87) | 7.85 (7.90) | 4.81 (4.77) |
| III-7 | H | i-Pr | H | 126.0–127.5 | 82.01 (82.04) | 8.15 (8.20) | 4.62 (4.56) |
| III-8 | H | i-Pr | H | 165.5–166.5 | 81.99 (82.04) | 8.22 (8.20) | 4.50 (4.56) |
| III-9 | H | Me | 4-Cl | 198.5–199.5 | 73.88 (73.78) | 7.14 (7.08) | 4.06 (4.10) |
| III-10 | Me | Me | H | 179.5–180.5 | 81.79 (81.87) | 7.85 (7.90) | 4.73 (4.77) |
| III-11 | Me | Me | 2-F | 179.0–179.5 | 77.19 (77.14) | 7.18 (7.12) | 4.46 (4.50) |
| III-12 | Me | Me | 4-F | 158.0–158.5 | 77.20 (77.14) | 7.09 (7.12) | 4.50 (4.50) |
| III-13 | Me | Me | 2-Cl | 138.0–138.5 | 73.22 (73.27) | 6.80 (6.76) | 4.32 (4.27) |
| III-14 | Me | Me | 3-Cl | 173.0–174.5 | 73.17 (73.27) | 6.77 (6.76) | 4.23 (4.27) |
| III-15 | Me | Me | 4-Cl | 174.0–175.0 | 73.32 (73.27) | 6.68 (6.76) | 4.25 (4.27) |
| III-16 | Me | Me | 4-Br | 173.0–174.0 | 64.61 (64.52) | 6.00 (5.96) | 3.81 (3.76) |
| III-17 | Me | Me | 2-Me | 141.5–143.0 | 81.95 (82.04) | 8.15 (8.20) | 4.51 (4.56) |

TABLE 3-continued

Compounds of the formula (1c)

| No. | R₁ | R₂ | X | Melting point, °C. | C, % | H, % | N, % |
|---|---|---|---|---|---|---|---|
| III-18 | Me | Me | 4-Me | 146.0–147.5 | 82.13 (82.04) | 8.16 (8.20) | 4.61 (4.56) |
| III-19 | Me | Me | 3-OMe | 131.0–131.5 | 78.10 (77.99) | 7.82 (7.79) | 4.29 (4.33) |
| III-20 | Me | Me | 4-OMe | 157.0–158.0 | 78.06 (77.99) | 7.85 (7.79) | 4.35 (4.33) |
| III-21 | Me | Et | H | 149.0–150.0 | 81.95 (82.04) | 8.16 (8.20) | 4.49 (4.56) |
| III-22 | Me | Et | 4-Cl | 140.0–141.0 | 73.66 (73.78) | 7.13 (7.08) | 4.06 (4.10) |

TABLE 4

Results of Infra-red Analysis

| No. | IR, cm⁻¹ |
|---|---|
| I-1 | 3288, 3026, 1643, 1541, 1216, 1029, 750, 698 |
| I-5 | 3306, 3030, 1646, 1545, 1496, 1223, 758, 749, 700 |
| I-6 | 3430, 2921, 1642, 1117, 754, 559 |
| I-7 | 3290, 1647, 1493, 1242, 751 |
| I-9 | 3288, 1645, 1544, 748 |
| I-10 | 3295, 1645, 1542, 1491, 1090, 747 |
| I-11 | 3400, 3260, 1647, 1540, 748, 694 |
| I-12 | 3279, 1650, 1547, 1488, 1205, 750 |
| I-13 | 3425, 1649, 1511, 1231, 554 |
| I-14 | 3427, 1650, 1035, 561 |
| I-15 | 3420, 3260, 1648, 1540, 749, 690 |
| I-16 | 3452, 3258, 1645, 1549, 753, 550 |
| I-17 | 3424, 3257, 2974, 1644, 1050 |
| I-18 | 3420, 1652, 1508, 759, 565 |
| I-19 | 3428, 1650, 1120, 620 |
| I-20 | 3274, 1647, 1544, 1224, 815, 750 |
| I-21 | 3433, 2924, 1650, 1120, 619 |
| I-22 | 3438, 3268, 1651, 1543, 1513, 1245, 1040, 755 |
| II-1 | 3284, 3276, 2928, 1648, 1642, 1527, 1297, 740, 696 |
| II-2 | 3278, 2936, 1643, 1611, 1519, 1493, 1093, 1016, 767 |
| II-4 | 3329, 2934, 1643, 1611, 1524, 783, 755 |
| II-5 | 3431, 3313, 2939, 1642, 1610, 1525, 1241, 1092, 753 |
| II-7 | 3269, 2954, 1642, 1609, 1539, 758, 702 |
| II-8 | 3427, 3301, 2963, 1641, 1607, 1584, 1491, 1091, 782 |
| II-9 | 3433, 2920, 1647, 1615, 1125 |
| II-10 | 3313, 1647, 1614, 1527, 1488, 1207, 782, 751 |
| II-11 | 3231, 3057, 2936, 1643, 1610, 1538, 1508, 1231, 833, 786 |
| II-12 | 3425, 3250, 2934, 1644, 1611, 1542, 1041, 757 |
| II-13 | 3307, 2936, 1646, 1613, 1528, 1298, 783, 753 |
| II-14 | 3424, 3280, 2925, 1645, 1612, 1104, 551 |
| II-15 | 3231, 3052, 1643, 1609, 1539, 1307, 1101, 1007, 787 |
| II-16 | 3434, 3259, 2936, 1645, 1913, 1536, 1301, 755 |
| II-17 | 3427, 3303, 2935, 1647, 1615, 1532, 1486, 1266, 1045 |
| II-18 | 3241, 1645, 1611, 1538, 1512, 1244, 1179, 1035, 835 |
| III-1 | 3243, 2938, 1644, 1548, 1496, 1237, 1031, 742, 725 |
| III-4 | 3262, 2928, 1644, 1539, 1232, 743 |
| III-5 | 3296, 2934, 1642, 1541, 1493, 1241, 751 |
| III-6 | 3286, 2932, 1641, 1543, 1225, 739, 700 |
| III-8 | 3422, 3283, 2933, 1640, 1547, 1228, 740, 700 |
| III-9 | 3418, 3265, 2933, 1601, 1549, 1494, 1228, 1089, 740 |
| III-10 | 3433, 3283, 2931, 1649, 1537, 1227, 738, 698, 550 |
| III-11 | 3284, 2934, 1648, 1544, 1206, 754, 737 |
| III-12 | 3270, 2936, 1643, 1545, 1510, 1231, 832, 743 |
| III-13 | 3432, 3300, 2928, 1645, 1541, 1038, 760 |
| III-14 | 3280, 2935, 1645, 1543, 1246, 1230, 1080, 780 |
| III-15 | 3433, 3273, 2933, 1646, 1548, 1104, 829, 740 |
| III-16 | 3434, 3301, 2930, 1649, 1526, 1224, 826, 741 |
| III-17 | 3303, 2936, 1648, 1542, 1493, 1450, 1058, 738, 722 |
| III-18 | 3286, 2930, 1648, 1536, 1227, 814 |
| III-19 | 3438, 3278, 2930, 1648, 1541, 1054 |
| III-20 | 3434, 3299, 2925, 1646, 1542, 1513, 1245, 1039 |

TABLE 5

Results of NMR Analysis

| No. | NMR [(CD₃)₂SO], δ |
|---|---|
| I-1 | 3.28–3.50(2H,m,C=CCH₂) 4.16–4.44(3H,m,CHCO,NCH₂) |

TABLE 5-continued

Results of NMR Analysis

| No. | NMR [(CD$_3$)$_2$SO], δ |
|---|---|
| | 5.63–6.33(2H,m,C=CH) 7.15(4H,s,⌬-H) |
| | 7.22(5H,s,⌬-H) 8.23–8.63(1H,t,NH) |
| I-2 | 3.26–3.52(2H,m,C=CCH$_2$) 4.19–4.48(3H,m,CHCO,NCH$_2$) |
| | 5.71–6.82(2H,m,C=CH) 7.01–7.51(8H,m,⌬-H) |
| | 8.22–8.63(1H,t,NH) |
| I-3 | 3.25–3.54(2H,m,C=CCH$_2$) 4.02–4.50(3H,m,CHCO,NCH$_2$) |
| | 5.72–6.33(2H,m,C=CH) 7.05–7.70(8H,m,⌬-H) |
| | 8.35–8.85(1H,t,NH) |
| I-4 | 3.25–3.49(2H,m,C=CCH$_2$) 4.07–4.45(3H,m,CHCO,NCH$_2$) |
| | 5.68–6.27(2H,m,C=CH) 7.14(4H,s,⌬-H) |
| | 7.25(4H,s,Cl-⌬-H) 8.30–8.66(1H,t,NH) |
| I-5 | 1.26–1.56(3H,d,CH$_3$) 3.16–3.46(2H,m,CH$_2$) |
| | 4.16–4.42(1H,q,CHCO) 4.54–5.12(1H,m,NCH) |
| | 5.60–6.70(2H,m,C=CH) 7.11(4H,s,⌬-H) |
| | 7.22(5H,s,⌬-H) 8.22–8.53(1H,d,NH) |
| I-6 | 1.35(3H,d,CH$_3$) 2.25(3H,s,⌬-CH$_3$) |
| | 3.10–3.48(2H,m,CH$_2$) 4.15–4.43(1H,q,CHCO) |
| | 4.84–5.21(1H,t,NCH) 5.52–6.34(2H,m,C=CH) |
| | 6.92–7.50(8H,m,⌬-H) 8.31–8.72(H,d,NH) |
| I-7 | 1.29(3H,d,CCH$_3$) 3.20–3.48(2H,m,CH$_2$) |
| | 3.73(3H,s,OCH$_3$) 4.17–4.44(1H,q,CHCO) |
| | 4.94–5.26(1H,t,NCH) 5.60–6.20(2H,m,C=CH) |
| | 6.77–7.38(8H,m,⌬-H) 8.17–8.48(1H,s,NH) |
| I-8 | 0.87(3H,t,CH$_3$) 1.06–1.95(4H,m,CH$_2$) |
| | 3.17–3.57(2H,m,C=CCH$_2$) 4.13–4.46(1H,q,CHCO) |
| | 4.45–4.95(1,m,NCH) 5.45–6.34(2H,m,C=CH) |
| | 6.90–7.60(9H,m,⌬-H) 8.25–8.65(1H,d,NH) |
| I-9 | 0.60–1.10(6H,m,CH$_3$) 1.67–2.23(1H,m, C\CH-C/C) |
| | 3.18–3.48(2H,m,CH$_2$) |
| | 4.22–4.71(2H,m,CHCO,NCH) 5.53–6.21(2H,m,C=CH) |
| | 6.93–7.41(9H,m,⌬-H) 8.20–8.59(1H,d,NH) |
| I-10 | 0.58–1.14(6H,q,CH$_3$) 1.63–2.30(1H,m, C\CH-C/C) |
| | 3.14–3.47(2H,m,CH$_2$) |
| | 4.22–4.70(2H,m,CHCO,NCH) 5.53–6.25(2H,m,C=CH) |
| | 6.94–7.50(8H,m,⌬-H) |
| | 8.30–8.60(1H,d,NH) |
| I-11 | 1.55(6H,s,CH$_3$) 3.15–3.43(2H,m,CH$_2$) |
| | 4.12–4.50(1H,q,CHCO) 5.68–6.22(2H,m,C=CH) |
| | 6.92–7.36(9H,m,⌬-H) 8.26(1H,s,NH) |
| I-12 | 1.64(6H,s,CH$_3$) 3.17–3.40(2H,m,CH$_2$) |
| | 4.21–4.47(1H,q,CHCO) 5.60–6.20(2H,m,C=CH) |
| | 6.74–7.42(8H,m,⌬-H) 8.32(1H,s,NH) |
| I-13 | 1.56(6H,s,CH$_3$) 3.14–3.47(2H,m,CH$_2$) |
| | 4.20–4.50(1H,q,CHCO) 5.68–6.23(2H,m,C=CH) |
| | 6.76–7.58(8H,m,⌬-H) 8.31(1H,s,NH) |
| I-14 | 1.67(6H,s,CH$_3$) 3.14–3.43(2H,m,CH$_2$) |
| | 4.22–4.48(1H,q,CHCO) 5.65–6.70(2H,m,C=CH) |
| | 6.97–7.75(8H,m,⌬-H) 8.40(1H,s,NH) |
| I-15 | 1.56(6H,s,CH$_3$) 3.18–3.42(2H,m,CH$_2$) |
| | 4.20–4.49(1H,q,CHCO) 5.66–6.24(2H,m,C=CH) |
| | 7.02–7.35(8H,m,⌬-H) 8.39(1H,s,NH) |
| I-16 | 1.53(6H,s,CH$_3$) 3.19–3.44(2H,m,CH$_2$) |
| | 4.17–4.48(1H,q,CHCO) 5.69–6.22(2H,m,C=CH) |
| | 7.15(4H,s,⌬-H) 7.26(4H,s,⌬-Cl) 8.39(1H,s,NH) |
| I-17 | 1.53(3H,s,CH$_3$) 3.19–3.48(2H,m,CH$_2$) |
| | 4.18–4.48(1H,q,CHCO) 5.66–6.22(2H,m,C=CH) |
| | 7.00–7.52(H,m,⌬-H) 8.29(1H,s,NH) |
| I-18 | 1.61(6H,s,CH$_3$) 2.43(3H,s,⌬-CH$_3$) |
| | 3.06–3.47(2H,m,CH$_2$) 4.17–4.46(1H,q,CHCO) |
| | 5.65–6.20(2H,m,C=CH) 6.80–7.50(8H,m,⌬-H) |
| | 8.25(1H,s,NH) |

TABLE 5-continued

| No. | Results of NMR Analysis NMR [(CD₃)₂SO], δ |
|---|---|
| I-19 | 1.56(6H,s,CH₃) 2.21(3H,s, 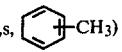—CH₃) 3.18–3.49(2H,m,CH₂) 4.22–4.49(1H,q,CHCO) 5.68–6.22(2H,m,C=CH) 6.81–7.43(8H,m, —H) 8.21(1H,s,NH) |
| I-20 | 1.54(6H,s,CH₃) 2.22(3H,s 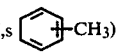—CH₃) 3.14–3.50(2H,m,C=CCH₂) 4.19–4.50(1H,q,CHCO) 5.58–6.26(2H,m,C=CH) 6.76–7.57(8H,m, —H) 8.19(1H,s,NH) |
| I-21 | 1.55(6H,s,CH₃) 3.19–3.41(2H,m,CH₂) 3.66(3H,s,OCH₃) 4.21–4.50(1H,q,CHCO) 5.58–6.27(2H,m,C=CH) 6.48–7.50(8H,m, —H) 8.24(1H,s,NH) |
| I-22 | 1.55(6H,s,CH₃) 3.19–3.41(2H,m,CH₂) 3.66(3H,s,OCH₃) 4.22–4.49(1H,q,CHCO) 5.60–6.28(2H,m,C=CH) 6.65–7.38(8H,m, —H) 8.16(1H,s,NH) |
| I-24 | 0.73(3H,t,CH₃) 1.49(3H,s,N—C—CH₃) 1.60–2.15(2H,m,N—C—CH₂) 3.18–3.45(2H,m,C=CCH₂) 4.25–4.55(1H,q,CHCO) 5.60–6.26(2H,m,C=CH) 7.13(4H,s, 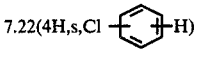—H) 7.22(4H,s,Cl—H) 8.08(1H,s,NH) |
| II-1 | 2.00–2.81(4H,m,CH₂CH₂) 4.37(2H,d,NCH₂) 6.28–6.50 (1H,t,C=CH) 7.06–7.44(9H,m, —H) 8.45–8.86(1H,t,NH) |
| II-2 | 1.94–2.90(4H,m,CH₂CH₂) 4.36(2H,d,NCH₂) 6.30–6.51 (1H,t,C=CH) 6.95–7.45(8H,m, —H) 8.55–8.88(1H,t,NH) |
| II-3 | 2.02–2.93(4H,m,CH₂CH₂) 4.35(2H,d,NCH₂) 6.30–6.53 (1H,t,C=CH) 6.99–7.45(8H,m, —H) 8.55–8.97(1H,t,NH) |
| II-4 | 1.26–1.53(3H,d,NCH₃) 1.98–2.97(4H,m,CH₂CH₂) 2.37(3H,s, 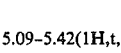—CH₃) 5.09–5.42(1H,t,NCH) 6.23–6.49 (1H,t,C=CH) 7.01–7.60(8H,m, —H) 8.45–8.78(1H,d,NH) |
| II-5 | 1.11–1.51(3H,d,CH₃) 2.05–2.91(4H,m,CH₂CH₂) 3.81(3H,s,OCH₃) 5.08–5.70(1H,m,NCH) 6.24–6.51 (1H,t,C=CH) 6.62–7.51(8H,m, —H) 8.25–8.65(1H,d,NH) |
| II-6 | 0.90(3H,t,CH₃) 1.12–1.99(4H,m,CH₂) 1.99–2.92 (4H,m,C=CCH₂CH₂) 4.65–5.20(1H,m,NCH) 6.18–6.43 (1H,t,C=CH) 7.00–7.55(9H,m, —H) 8.38–8.72(1H,d,NH) |
| II-7 | 0.52–1.15(6H,q,CH₃) 1.70–2.92(5H,m,NCCH,CH₂CH₂) 4.46–4.84(1H,t,NCH) 6.14–6.42(1H,t,C=CH) 6.85–7.47(9H,m, —H) 8.37–8.86(1H,d,NH) |
| II-8 | 0.60–1.15(6H,q,CH₃) 1.62–2.91(5H,m,NCCH,CH₂CH₂) 4.34–4.81(1H,t,NCH) 6.17–6.38(1H,t,C=CH) 7.15 (4H,s, —H) 7.35(4H,s, —Cl) 8.43–8.73(1H,d,NH) |
| II-9 | 1.63(6H,s,CH₃) 1.90–2.95(4H,m,CH₂CH₂) 6.28–6.50 (1H,t,C=CH) 7.00–7.62(9H,m, —H) 8.28(1H,s,NH) |
| II-10 | 1.70(6H,s,CH₃) 2.01–2.92(4H,m,CH₂CH₂) 6.24–6.47(1H,t,C=CH) 6.82–7.60(8H,m, —H) 8.34(1H,s,NH) |
| II-11 | 1.63(6H,s,CH₃) 2.05–2.90(4H,m,CH₂CH₂) 6.27–6.48(1H,t,C=CH) 6.89–7.60(8H,m, —H) 8.30(1H,s,NH) |
| II-12 | 1.77(6H,s,CH₃) 2.02–3.00(4H,m,CH₂CH₂) 6.33–6.58(1H,t,C=CH) 7.01–7.73(8H,m, —H) 8.43(1H,s,NH) |
| II-13 | 1.62(6H,s,CH₃) 1.95–2.98(4H,m,CH₂CH₂) 6.28–6.50(1H,t,C=CH) 7.05–7.50(8H,m, —H) 8.40(1H,s,NH) |
| II-14 | 1.61(6H,s,CH₃) 1.95–3.00(4H,m,CH₂CH₂) 6.27–6.48(1H,t,C=CH) 7.12(4H,s, —H) 7.34(4H,s, —Cl) 8.34(1H,s,NH) |
| II-15 | 1.62(6H,s,CH₃) 2.05–2.92(4H,m,CH₂CH₂) 6.26–6.50(1H,t,C=CH) 6.98–7.12(8H,m, —H) |

TABLE 5-continued

| No. | Results of NMR Analysis<br>NMR [(CD₃)₂SO], δ |
|---|---|
| II-16 | 8.33(1H,s,NH)<br>1.70(6H,s,CH₃) 1.95–2.96(4H,m,CH₂CH₂)<br>2.44(3H,s, –CH₃) 6.25–6.47(1H,t,C=CH)<br>6.80–7.65(8H,m, –H) 8.35(1H,s,NH) |
| II-17 | 1.62(6H,s,CH₃) 2.05–2.90(4H,m,CH₂CH₂)<br>3.73(3H,S,OCH₃) 6.25–6.47(1H,t,C=CH)<br>6.50–7.31(8H,m, –H) 8.27(1H,s,NH) |
| II-18 | 1.63(6H,s,CH₃) 2.03–2.93(4H,m,CH₂CH₂)<br>3.72(3H,S,OCH₃) 6.23–6.49(1H,t,C=CH)<br>6.65–7.44(8H,m, –H) 8.19(1H,s,NH) |
| III-1 | 1.60–2.16(4H,m,CH₂CH₂) 2.57–2.87(2H,t, –CH₂)<br>4.29(2H,d,NCH₂) 7.01(4H,s, –H)<br>7.26(4H,s,– –H) 8.25–8.62(1H,t,NH) |
| III-2 | 1.32–2.13(4H,m,CH₂CH₂) 2.38–2.87(2H,m, –CH₂)<br>3.53–3.91(1H,t,CHCO) 4.35(2H,d,NCH₂)<br>6.80–7.60(8H,m, –H) 8.30–8.70(1H,t,NH) |
| III-3 | 1.61–2.13(4H,m,CH₂CH₂) 2.54–2.85(2H,t, –CH₃)<br>4.26(2H,d,NCH₂) 7.03(4H,s, –H)<br>7.30(4H,s,Cl– –H) 8.30–8.68(1H,t,NH) |
| III-4 | 1.22–1.49(3H,m,NCCH₃) 1.57–2.05(4H,m,CH₂CH₂)<br>2.29(3H,s,CH₃) 2.35–2.86(2H,t, –CH₂)<br>3.42–3.82(1H,t,CHCO) 4.80–5.30(1H,m,NCH)<br>6.62–7.52(8H,m, –H) 8.20–8.60(1H,d,NH) |
| III-5 | 1.19–1.46(3H,d,CCH₃) 1.60–2.20(4H,m,CH₂CH₂)<br>2.38–2.87(2H,t, –CH₂) 3.76(3H,s,OCH₃) 5.04–5.41 |

TABLE 5-continued

| No. | Results of NMR Analysis<br>NMR [(CD₃)₂SO], δ |
|---|---|
| | (1H,t,NCH) 6.70–7.47(8H,m, –H) 8.08–8.45(1H,d,NH) |
| III-6 | 0.69–1.17(3H,m,CH₃) 1.40–2.20(4H,m,CH₂ch₂)<br>2.39–2.87(2H,t, –CH₂) 3.54–3.89(1H,t,CHCO)<br>4.48–4.96(1H,q,NCH) 6.80–7.42(9H,m, –H)<br>8.25–8.57(1H,d,NH) |
| III-7 | 0.69(3H,t,CH₃) 1.10–2.25(6H,m,CH₂) 2.35–2.90<br>(2H,m, –CH₂) 3.42–3.92(1H,m,CHCO) 4.55–5.08<br>(1H,m,NCH) 6.76–7.61(9H,m, –H) 8.25–8.69(1H,d,NH) |
| III-8 | 0.62–1.10(6H,m,CH₃) 1.47–2.18(4H,m,CH₂CH₂)<br>2.37–2.88(2H,t, –CH₂) 3.55–3.92(1H,t,CHCO)<br>4.32–4.75(1H,t,NCH) 6.69–7.42(9H,m, –H)<br>8.19–8.49(1H,d,NH) |
| III-9 | 0.64–1.08(6H,m,CH₃) 1.53–2.17(4H,m,CH₂CH₂)<br>2.38–2.86(2H,t, –CH₂) 3.55–3.91(1H,t,CHCO)<br>4.32–4.76(1H,t,NCH) 6.70–7.45(9H,m, –H)<br>8.00–8.38(1H,d,NH) |
| III-10 | 1.58(6H,s,CH₃) 1.30–2.20(4H,m,CH₂CH₂)<br>2.32–2.83(2H,m, –CH₂) 3.50–3.93(1H,t,CHCO)<br>6.82–7.50(9H,m, –H) 8.12(1H,s,NH) |
| III-11 | 1.67(3H,s,CH₃) 1.48–2.06(4H,m,CH₂CH₂)<br>2.36–2.84(2H,t, –CH₂) 3.50–3.92(1H,t,CHCO)<br>6.78–7.50(8H,m, –H) 8.27(1H,s,NH) |
| III-12 | 1.56(6H,d,CH₃) 1.48–2.10(4H,m,CH₂CH₂)<br>2.37–2.82(2H,t, –CH₂) 3.52–3.89(1H,t,CHCO)<br>6.60–7.73(8H,m, –H) 8.21(1H,s,NH) |
| III-13 | 1.71(6H,d,CH₃) 1.34–2.11(4H,m,CH₂CH₂) |

TABLE 5-continued

Results of NMR Analysis

| No. | NMR [(CD₃)₂SO], δ |
|---|---|
| | 2.32–2.81(2H,m, ⟨⟩–CH₂) 3.52–3.93(1H,t,CHCO) |
| | 6.77–7.64(8H,m, ⟨⟩–H) 8.34(1H,s,NH) |
| III-14 | 1.58(6H,s,CH₃) 1.67–2.10(4H,m,CH₂CH₂) |
| | 2.37–2.84(2H,m, ⟨⟩–CH₂) 3.55–3.90(1H,t,CHCO) |
| | 6.87–7.42(8H,m, ⟨⟩–H) 8.36(1H,s,NH) |
| III-15 | 1.56(6H,d,CH₃) 1.36–2.20(4H,m,CH₂CH₂) |
| | 2.38–2.82(2H,m, ⟨⟩–CH₂) 3.55–3.87(1H,t,CHCO) |
| | 7.04(4H,s, ⟨⟩–H) 7.29(4H,s,Cl–⟨⟩–H) |
| | 8.29(1H,s,NH) |
| III-16 | 1.57(6H,d,CH₃) 1.37–2.20(4H,m,CH₂CH₂) |
| | 2.37–2.87(2H,t, ⟨⟩–CH₂) 3.53–3.87(1H,t,CHCO) |
| | 6.90–7.63(8H,m, ⟨⟩–H) 8.21(1H,s,NH) |
| III-17 | 1.65(9H,d,CH₃) 1.35–2.15(4H,m,CH₂CH₂) 2.46 |
| | (3H,s, ⟨⟩–CH₂) 2.38–2.88(2H,m, ⟨⟩–CH₂) 3.57–3.90 |
| | (1H,q,CHCO) 6.84–7.60(8H,m, ⟨⟩–H) 8.23(1H,s,NH) |
| III-18 | 1.55(6H,d,CH₃) 1.33–2.16(4H,m,CH₂CH₂) 2.22 |
| | (3H,s, ⟨⟩–CH₂) 2.38–2.85(2H,m, ⟨⟩–CH₂) 3.50–3.90 |
| | (1H,q,CHCO) 6.85–7.73(8H,m, ⟨⟩–H) 8.14(1H,s,NH) |
| III-19 | 1.57(6H,d,CH₃) 1.35–2.22(4H,m,CH₂CH) 3.69(3H,s,OCH₃) 3.41–3.89(1H,m,CHCO) |
| | 6.45–7.35(8H,m, ⟨⟩–H) 8.19(1H,s,NH) |
| III-20 | 1.56(6H,d,CH₃) 1.33–2.19(4H,m,CH₂CH₂) 2.34– |
| | 2.82(2H,t, ⟨⟩–CH₂) 3.70(3H,s,OCH₃) 3.50–3.89 |
| | (1H,m,CHCO) 6.64–7.41(8H,m, ⟨⟩–H) 8.10(1H,s,NH) |
| III-22 | 0.76(3H,t,CH₃) 1.54(3H,s,N—C—CH₃) 1.30–2.25 |
| | (6H,m,CH₂) 2.36–2.86(2H,m, ⟨⟩–CH₂) 3.50–4.00 |
| | (1H,m,CHCO) 7.03(4H,s, )S 8.06(1H,s,NH) |

Preferred compounds of the present invention include Compound Nos. I-5 to I-24, II-4 to II-18 and III-5 to III-22. More preferred compounds include Compound Nos. I-11 to I-24, II-9 to II-18 and III-10 to III-22. Particularly preferred compounds are Nos. I-11, I-13, I-15, I-16, II-9, II-11, II-13, III-10, III-12, III-15, III-21 and III-22.

The amide compounds of the present invention can be prepared by various methods. One such method of preparation is as follows. A compound of the formula:

$$R-CO-Y \qquad (2)$$

is reacted with an amine of the formula:

$$H_2N-\underset{\underset{R_2}{|}}{\overset{\overset{R_1}{|}}{C}}-Ar-X \qquad (3)$$

wherein R is 1,2,3,4-tetrahydro-1-naphthyl, 1,4-dihydro-1-naphthyl or 3,4-dihydro-1-naphthyl; $R_1$ is hydrogen or methyl; $R_2$ is hydrogen, methyl, ethyl, nopropyl or isopropyl; Ar is a phenylene group; X is hydrogen, a halogen such as fluorine, chlorine or bromine, methyl or methoxy; and Y is a halogen or $-OR_3$, said $R_3$ being hydrogen or an alkyl containing 1–30 carbon atoms.

In an example of this reaction 1,4-dihydro-alpha-naphthoic acid is reacted with thionyl chloride at room temperature for 1–6 hours to obtain 1,4-dihydro-alpha-naphthoic chloride. This compound is then reacted with an amine of the formula (3) and triethylamine in ether solvent under reflux for 0.1–3 hours to obtain a compound of the formula (1a). Compounds of the formulae (1b) and (1c) may also be produced in the same manner as just described using 3,4-dihydro-alpha-naphthoic acid and 1,2,3,4-tetrahydro-alpha-naphthoic acid, respectively as starting materials.

In another method of synthesis, 1,4-dihydro-alpha-naphthoic acid is dissolved in methylene chloride; and then to this solution is added an amine of the formula (3), triethylamine and N-methyl-2-chloro-pyridinium iodide. The mixture is then heated under reflux for 0.5–2 hours whereby a compound of formula (a) is obtained. Compounds of the formulae (1b) and (1c) may also be prepared similarly.

Object amide compounds may be isolated from the resulting mixture by known methods. For instance, 5% aqueous hydrochloric acid is added to the reaction product, and the solvent is removed under reduced pressure. Thereafter, the resulting precipitated compound is separated by filtration and dried. The compound is then recrystallized from a solvent such as methanol, ether, benzene or the like to obtain the object compound.

1,2,3,4-Tetrahydro-1-naphthoic acid, which is useful as the raw material for the preparation of the amide compounds of formula (1c), can be economically produced by reacting 1,2,3,4-tetrahydro-1-naphthyl sodium with carbon dioxide.

1,2,3,4-Tetrahydro-1-naphthyl sodium is preferably obtained by transmetalation of tetralin with phenyl sodium. Other organosodium compounds such as methylsodium, vinylsodium, ethylsodium, n-propylsodium, 3-methylphenyl-sodium, 4-methylphenylsodium, naphthyl-1-sodium and the like, may also be used for transmetalation. Phenylsodium is the preferred organosodium. In fact, the use of the organo-sodium reagent in the present specification is shown in terms of phenylsodium.

In the transmetalation reaction, tetralin is generally used in an amount of at least 1 mole, preferably 1–10 moles, per mole of phenylsodium.

The reaction of tetralin with phenylsodium proceeds very slowly without an accelerator. Accordingly, the reaction is generally conducted in the presence of an accelerator. Examples of suitable accelerators are tertiary amines including acyclic tertiary amines such as tetramethylethylenediamine, triethylamine and the like; and cyclic amines such as 2,2'-bipyridine, N-methylimidazole, dimethylaniline, N-methylpiperidine, N-methylmorpholine, 1,10-phenanthroline and the like; tri-substituted phosphines such as triphenylphosphine, 1,2-bis(diphenylphosphino)-ethane and the like; and polyethers such as dimethoxyethane, diglyme, triglyme and the like. Of these materials the tertiary amines are preferred and in particular tetramethylethylenediamine. The amount of the accelerator employed usually ranges from 0.1–5 moles, preferably 0.5–2 moles, per mole of phenylsodium. The reaction temperature is generally about $-20°$ C. to about $50°$ C., preferably about $0°$ C. to about $20°$ C.

Phenysodium can be produced according to known methods such as the method disclosed in "Reagents for Organic Synthesis", page 848, published by John Wiley and Sons Inc. In this method chlorobenzene is reacted with particulate metallic sodium dispersed in a solvent. Suitable dispersing mediums include, for example, aliphatic hydrocarbons such as gas oil, mineral spirit, n-octane and isooctane; and aromatic hydrocarbons such as tetralin and biphenyl, and so on. Of these solvents tetralin, is the preferred solvent since it is also a reactant.

Phenylsodium is used in an amount of generally 0.5–60%, preferably 5–30%. The reaction time is usually 0.1–5 hours, preferably 0.5–2 hours.

1,2,3,4-Tetrahydro-1-naphthylsodium can be obtained in the state of being dispersed in the solvent used in preparation of phenylsodium. The fact that 1,2,3,4-tetrahydro-1-naphthylsodium is formed can be confirmed by treating the medium containing the compound with methyl iodide and observing the formation of 1-methyltetralin.

In the preparation of 1,2,3,4-tetrahydro-1-naphthoic acid, 1,2,3,4-tetrahydro-1-naphthylsodium can be reacted with gaseous carbon dioxide which is present in a bomb or with dry ice. Carbon dioxide is generally used in an amount of at least 1 mole, preferably 1–10 moles, per mole of 1,2,3,4-tetrahydro-1-naphthylsodium.

The order of addition of 1,2,3,4-tetrahydro-1-naphthylsodium and carbon dioxide is not particularly important. Thus, for example, in one method carbon dioxide gas can be introduced into a dispersion of 1,2,3,4-tetrahydro-1-naphthylsodium. In a second method a dispersion of 1,2,3,4-tetrahydro-1-naphthylsodium can be added to a solution containing carbon dioxide dissolved therein, prepared before-hand by introducing carbon dioxide gas into a solvent such as diethyl ether, tetralin or the like. In a third method 1,2,3,4-tetrahydro-1-naphthylsodium can be placed on dry ice. Of these methods the second method is preferred.

The reaction of 1,2,3,4-tetrahydro-1-naphthylsodium and carbon dioxide is exothermic. The reaction temperature, which can be controlled by external cooling and by the speed of addition of the reagents is usually about $-50°$ C. to about $50°$ C., preferably about $0°$ C. to about $20°$ C. The reaction time is usually 0.5–10 hours, preferably 1–5 hours. The reaction may be carried out under pressure, which is usually up to 5 kg/cm, or under normal pressure.

After the reaction, the resulting sodium 1,2,3,4-tetrahydro-1-naphthoate product is extracted with an aqueous alkaline solution, and then the extract is treated with an acid such as hydrochloric acid, sulfuric acid or the like to convert the salt into the free carboxylic acid. The solution is then filtered or extracted with an organic solvent such as toluene and then, if necessary, the acid is recrystallized from a mixture of methanol and water to obtain 1,2,3,4-tetrahydro-1-naphthoic acid.

The compound of formula (1) of the present invention has herbicidal activity which is selective to weeds which grow not only in dry fields (farm land) but also wet fields (paddy fields). The compound exhibits substantially no or reduced phytotoxicity to crops including aquatic or waterfield rice, and dry field crops such as various grains, pulses, cotton plants, vegetables and the like.

Wetfield weeds which are affected by the present compound include Compositae such as *Bidens tripartita;* Scrophulariaceae such as *Deinostema violacea, Dopatrium junceum, Vandellia angustifolia* and *Lindernia pyxidaria;* Lythraceae such as *Ammannia multiflora, Rotala indica* and *Lythrum anceps;* Elatinaceae such as *Elatine triandra;* Callitrichaceae such as *Callitriche verna;* Oenotheraceae such as *Ludwigia prostrata;* Polygonaceae such as *Polygonum hydropiper;* Pontederiaceae such as *Monochoria vaginalis;* Eriocaulaceae such as *Eriocaulon sieboldianum* and *Eliocaulon miquelianum;* Lemnaceae such as *Spirodela polyrhiza, Lemna trisulka* and *Lemna paucicostata;* Cyperaceae such as *Fimbristylis miliaceae, Scirpus juncoides* Roxs.c-.subsp.hotarui, *Cyperus difformis* and *Eleocharis acicularis;* Gramineae such as *Hymenachne indica* Buse form.indica and *Echinochloa crus-galli;* Hydrocharitaceae such as *Blyxa sessilis* and *Ottelia japonica;* Alismataceae such as *Alisma canaliculatum;* Marsileaceae such as *Marsilea quadrifolia;* and Zygnemataceae such as *Spirogyra arcla.*

Dry field weeds which are affected by the present compound include Chenopodiaceae such as *Chenopodium serotinum;* Cruciferae such as *Capsella bursa-pastoris, Raphanus raphanistrum* and *Brassica kabar;* Amaranthaceae such as *Amaranthus viridis;* Polygonaceae such as *Rumex japonicus* and *Polygonum persicaria;* Rubiaceae such as *Galium aparine;* Caryophyllaceae such as *Cerastium holosteoides* var. angustifolium, *Stellaria alsine* var. undulata and *Stellaria media;* Scrophulariaceae such as *Veronica didyma;* Compositae such as *Erigeron philadelphicus, Erigeron candensis, Taraxacum officinale* and *Matricaria chamomilla;* Convolvulaceae such as *Calystegia hederacea;* Oxalidaceae such as *Oxalis corniculata;* Gramineae such as *Alopecurusaequalis* var. amurensis, *Poa annua* and *Digitaria adscendens;* Euphorbiaceae such as *Euphorbia supina;* Solanaceae such as *Solanum nigrum;* and Cyperaceae such as *Cyperus iria.*

In herbicidal compositions containing at least one embodiment of the amide compound of formula (1) of the present invention, the composition may contain at least one other herbicide (II), if necessary.

Illustrative examples of other suitable herbicides (II) include the following:

(N) Phenoxy-type herbicides:
  (N-1) 2,4-dichlorophenoxyacetic acid,
  (N-2) (4-chloro-o-tolyloxy)acetic acid,
  (N-3) 2-(2-naphthyloxy)propionanilide
(Q) Diphenylether-type herbicides:
  (Q-1) 2,4-dichloro-1-(4-nitrophenoxy)benzene,
  (Q-2) methyl-5-(2,4-dichlorophenoxy)-2-nitrobenzoate,
  (Q-3) 2,4-dichloro-1-(3-methoxy-4-nitrophenoxy)benzene
(T) Amide-type herbicides:
  (T-1) N-butoxymethyl-2-chloro-2′,6′-diethylacetonitrile
  (T-2) 2-chloro-2′,6′-diethyl-N-methoxymethylacetoanilide
  (T-3) N-(alpha,alpha-dimethylbenzyl)-alpha-bromo-t-butyl acetoamide
(U) Carbamate-type herbicides:
  (U-1) S-(4-chlorobenzyl)N,N-diethyl thiocarbamate,
  (U-2) S-ethylperhydroazepine-1-carbothioate
(V) Diazole-type herbicides:
  (V-1) 5-t-butyl-3-(2,4-dichloro-5-isopropoxyphenyl)-1,3,4-oxadiazole-2(3H)-one
(W) Pyrazole-type herbicides:
  (W-1) 4-(2,4-dichlorobenzoyl)-1,3-dimethylpyrazole-5-yl-4-toluene sulfonate
  (W-2) 4-(2,4-dichlorobenzoyl)-1,3-dimethyl-5-phenacyloxy pyrazole
(Y) Urea-type herbicides:
  (Y-1) 1-(alpha,alpha-dimethylbenzyl)-3-(p-tolyl)urea,
  (Y-2) 1-(alpha,alpha-dimethylbenzyl)-3-phenylurea
(Z) Triazine-type herbicides:
  (Z-1) 2-chloro-4,6-bis(ethylamino)-1,3,5-triazine
  (Z-2) 2-chloro-4-ethylamino-6-isopropylamine-1,3,5-triazine
  (Z-3) 2,4-bis(ethylamino)-6-methylthio-1,3,5-triazine Of these compounds the preferred are (N), (Q), (T), (U) and (W), particularly (N-3), (Q-3), (T-1), (U-1), (U-2) and (W-1).

The weight ratio of said amide compound (I) to one or more other herbicides (II) can vary widely. For instance, (I) may be used in such an amount of 1–99% or greater, preferably 20–80%, based on the total weight of the active ingredient [(I)+(II)].

In herbicidal compositions according to the invention, the active ingredient [(I) and optionally (II)] may be admixed with one or more adjuvants, include the likes of solid or liquid extenders, carriers, diluents, conditioning agents, surfactants, water-soluble polymers and other additives.

Surfactants which can be used in herbicidal formulations are well known to those skilled in the art and have been well documented in U.S. or other foreign patents, bulletins and textbooks. Surfactants which can be used for the purpose of emulsifying, dispersing, wetting, diffusing, spreading, binding, controlling degradability, stabilyzing active ingredients, improving flowability, rust prevention and so on, include nonionic, anionic, cationic and amphoteric agents and combinations of two or more of these surfactant types. Of the surfactants the preferred are nonionic and anionic agents, and combinations of these surfactants.

Examples of suitable surfactants include the following:

(a) Nonionic surfactants:
  i. polyoxyalkylene-type surfactants such as polyoxyalkylene alkylaryl ethers, polyoxyethylene polyoxypropylene polyols, polyoxyalkylene alkyl ethers, polyoxyalkylene polyhydric alcohol fatty esters, polyoxyalkylene polycyclic ethers such as polyoxyalkylene styrenated aryl ethers, polyoxyalkylene fatty esters, polyoxyalkylene alkylamines, polyoxyalkylene alkylmercaptans and the like; and
  ii. Polyhydric alcohol-type surfactants such as polyhydric alcohol fatty esters and the like.

Of these nonionic surfactants the preferred are polyoxyalkylene alkylaryl ethers, polyoxyethylene polyoxypropylene polyols, polyoxyalkylene alkyl ethers, polyoxyalkylene polyhydric alcohol fatty esters, polyoxyalkylene styrenated aryl ethers and polyoxyalkylene fatty esters. More preferred surfactants are polyoxyalkylene alkylaryl ethers, particularly polyoxyethylene nonylphenyl ethers and polyoxyethylene polyoxypropylene polyols particularly polyoxyethylated polypropyleneglycols.

(b) Anionic surfactants:
  i. Sulfate ester-type surfactants such as salts of alkyl sulfates, polyoxyalkylene alkyl sulfates, polyoxyalkylene alkylarylether sulfates, fatty ester sulfates, fatty acid alkylol amide sulfates, sulfated oils, highly sulfated oils, sulfated fatty esters, sulfated fatty acids, sulfated olefins and the like;
  ii. Sulfonic acid-type surfactants such as salts of alkylbenzene sulfonic acids, (alkyl)naphthalene sulfonic acids and formalin condensates thereof, sulfo-succinates such as dialkylsulfosuccinate, alkane sulfonic acids, alhpa-olefin sulfonic acids, fatty amide sulfonic acids, lignin sulfonic acids, petroleum sulfonic acids and the like;
  iii. Phosphate ester-type surfactants such as salts of alkyl phosphates, polyoxyalkylene alkylether phosphates, polyoxyalkylene alkylarylether phosphates and the like; and
  iv. Carboxylic acid-type surfactants such as salts of fatty acids and the like.

Of these anionic surfactants the preferred are salts of alkyl sulfates, polyoxyalkylene alkylarylether sulfates, alkylbenzene sulfonic acids, alkylnaphthalene sulfonic acids, sulfosuccinates, lignin sulfonic acids, alkyl phosphates, fatty acid alkylol amide sulfates and fatty amide sulfonic acids. More preferred surfactants are salts of alkyl sulfates, polyoxyalkylene alkylarylether sulfates, alkylbenzene sulfonic acids, alkylnaphthalene sulfonic acids, sulfosuccinates and lignin sulfonic acids. Preferred salts include the alkali and alkaline earth salts.

(c) Cationic surfactants:
  i. Quaternary ammonium salt-type surfactants such as alkyl ammonium salts, aryl alkyl ammonium salts, heterocyclic ammonium salts such as pyridinium salts and imidazolinium salts and the like; and (d) Amphoteric surfactants:
  i. Carboxylate-type amphoteric surfactants,
  ii. Sulfate-type amphoteric surfactants,
  iii. Sulfonate-type amphoteric surfactants,
  iv. Phosphate-type amphoteric surfactants.

Typical examples of these surfactants are described in U.S. Pat. No. 4,332,447 and in U.S. patent application, Ser. No. 495,833, filed May 18, 1983.

Water-soluble polymers which act as assistants for dispersions and suspensions and for spreading include natural, semisynthetic and synthetic polymers.

Examples of suitable natural water-soluble polymers include gum arabic, pectic acid, gum tragacanth, guar gum, alginic acid salts, chitosan and the like.

Examples of suitable semisynthetic water-soluble polymers include cellulosic resins, for example, etherified celluloses, such as carboxymethyl cellulose salts, methyl cellulose, ethyl cellulose, cyanoethyl cellulose, hydroxyethyl or hydroxypropyl cellulose and the like, and esterified celluloses such as cellulose sulfate and the like; as well as the corresponding starch derivatives such as carboxymethyl starch salts.

Suitable synthetic water-soluble polymers include, for example, acrylic resins, including anionic types such as polyacrylic acid salts, partially hydrolyzed polyacrylamides, copolymers of acrylamide and vinyl sulfonic acid salts and the like, nonionic types such as polyacrylamide, poly(hydroxyethyl acrylate) and the like, and cationic types such as dialkylaminoalkyl (meth)acrylate polymers, salts thereof, quaternary ammonium salts thereof and the like; polyvinylalcohol, poly(ethylene oxide), polyvinylpyrrolidone, polyvinylpyridine, polyvinylimidazoline, dimethyldiallylammonium chloride cyclized polymers and the like.

Definite examples of water-soluble polymers may be found in "WATER-SOLUBLE POLYMERS Technology and Applications" (Noyes Data Corp. 1976).

These water-soluble polymers have molecular weights of usually at least 2,000, preferably 5,000–200,000 or higher.

Of these polymers the preferred are natural water-soluble polymers, etherified celluloses, acrylic resins, polyvinylalcohol and polyvinylpyrrolidone. More preferred polymers are alginic acid, carboxymethyl cellulose salts, acrylic resins, polyvinylalcohol and polyvinylpyrrolidone.

The carriers which are optionally used in herbicidal compositions include solid, liquid and gaseous types.

Illustrative of suitable solid carriers are:

i. inorganic substances, for example, talcs, clays, such as kaolin, kaolinites, attapulgites, montmorillonites, bentonite, Fuller's earth and the like, diatomaceous earth, pyrophyllite, calcium carbonate, magnesium carbonate, potassium chlorate, niter, apatite, zeolite, alumina, silicic anhydride, mica, vermiculite, gypsum, and so on; and ii. organic substances, for instance, plant and vegetable source materials such as flours of wood, soya bean, tobacco, walnut shell, wheat and cottonseed, starch and crystalline cellulose; waxes such as carnauba wax and beeswax; resins such as polyvinylchlorides, cumarone resins, petroleum resins, alkyd resins, polyalkyleneglycols, ketone resins, ester gum, copal gum, dammar gum, and the like.

Of the solid carriers the preferred are clays such as kaolin, kaolinites and montmorillonites, silicic anhydride, diatomaceous earth, calcium carbonate, potassium chlorate and resins. More preferred are clays such as kaolin, kaolinites and montmorillonites, silicic anhydride, diatomaceous earth and calcium carbonate.

Suitable liquid carriers include, for example, aromatic hydrocarbons such as benzene, toluene, xylene, ethylbenzene, cumene, methylnaphthalene and the like; paraffinic and naphthenic hydrocarbons such as kerosene, mineral oil, spindle oil, white oil and the like; chlorinated hydrocarbons such as carbon tetrachloride, chloroform, trichloroethylene, monochlorobenzene, o-chlorotoluene and the like; ethers such as dioxane, tetrahydrofuran and the like; ketones such as acetone, methyl ethyl ketone, diiso-butyl ketone, cyclohexanone, acetophenone, isophorone and the like; esters such as ethyl acetate, amyl acetate, ethyleneglycol acetate, diethyleneglycol acetate, dibutyl maleate, diethyl succinate and the like; alcohols such as methanol, n-hexanol, ethyleneglycol, propyleneglycol, cyclohexanol, benzyl alcohol and the like; ether alcohols such as ethyleneglycol ethyl ether, ethyleneglycol phenyl ether, diethyleneglycol ethyl ether, diethyleneglycol butyl ether and the like; polar solvents such as dimethyl formamide, dimethyl sulfoxide and the like; and water.

Of the liquid carriers the preferred are aromatic hydrocarbons, ketones, alcohols, ether alcohols, polar solvents, water and esters. More preferred liquid carriers are aromatic hydrocarbons, ketones, polar solvents and water.

Examples of gaseous carriers are carbon dioxide, freons, propane, butane and the like.

The herbicidal compositions may contain, if necessary, other materials, for instance, agrochemicals such as insecticides, fungicides, nematocides, rodenticides, plant growth regulators, repellants and attractants; fertilizers such as urea, ammonium sulfate, ammonium phosphate and potassium salts; soil conditioners, antifreezing agents, mildewproofing agents, colorants, antifoamers, flow improvers, anticaking agents and the like.

The amount and kind of additives selected for a formulation is determined by the end use of the product and the desired properties of the formulation.

The herbicidal compositions of the invention may be solid or liquid, and include both dilute and concentrated compositions which require dilution before use.

In general, herbicidal compositions of the present invention contain (1) usually 0.5–90%, preferably, 1–80% of the active ingredient [said amide compound (I) or combination thereof with the other herbicide (II)];
(2) usually 0.1–20%, preferably 0.5–15% of surfactant, water-soluble polymer or combination of these ingredients;
(3) usually 0–99%, preferably 10–90% of carrier; and
(4) usually 0–20%, preferably 0–10% of other additives. based on the total weight of the composition.

Concentrated compositions may contain generally 20–99%, preferably 20–90% of the active ingredient; while diluted compositions ready for use contain usually 0.01–5%, preferably 0.02–2% of the active ingredient.

Herbicidal formulations include wettable powders, granules, dust formulations, flowable formulations, suspensions in water, in organic solvents and in mixtures of water and water-miscible organic solvents, emulsifiable concentrates and solutions in solvents; as well as aerosols.

Preparations, formulations and particle size of these formulations are well known to those skilled in the art and are well documented.

For example, granule formulations contain (1) preferably 0.5–50%, particularly 0.1–15% of the active ingredient; (2) preferably 0.1–15%, particularly 0.5–10% of surfactant, (3) preferably 0.1–5%, particularly 0.5–2% of water-soluble polymer; and (4) preferably 30–99%, particularly 70–95% of carrier, based on the total weight of the composition.

Granule or particulate formulations can be produced by adding a liquid to the above-mentioned components, treating the mixture mechanically, and then usually drying the material. For instance, appropriate components can be charged into a kneader and then a proper amount of water is added, followed by granulating the mixture to a particle size range of 0.5-1 mm with a granulator such as a screw extrusion granulator or a basket-type granulator. Thereafter, the resulting granules are dried in a drier, such as a continuous fluidized drier, followed by regulating the granules to length of 1-2 mm to obtain a final product in the form of granules. Alternatively, a solution, a suspension or a melt of the active ingredient can be sprayed on the surface of performed granules of a carrier.

Wettable powders contain (1) preferably 10-90%, particularly 30-80% of the active ingredient; (2) preferably 1-15%, particularly 3-13% of surfactant and (3) preferably 5-70%, particularly 10-70% of carrier based on the total weight of the composition.

Wettable powders can be prepared by blending and grinding the above components. It is preferred to coarsely divide the active ingredients and the carriers blended beforehand, followed by finely grinding the resultant coarse granules to a particle size range of 1-5 micron with a pulverizer such as a jetmill, a micron mill, an atomizer or the like and then to mix the fine particles with the surfactants.

Flowable formulations contains (1) preferably 1-80%, particularly 10-70% of the active ingredient; (2) preferably 0.1-15%, particularly 0.5-10% of surfactant, (3) preferably 1-20%, particularly 5-15% of water-soluble polymer; and (4) preferably 5-90%, particularly 10-85% of carrier based on the total weight of the composition.

In the case of flowable formulations, it is preferred to use, at least as a part of the water-soluble polymers, thickeners or polymers of thickening power, for example, natural water-soluble polymers such as gum tragacanth, guar gum, alginic acid salts; cellulosic resins such as carboxymethyl cellulose salts, methyl cellulose, and carboxymethyl starch salts; and acrylic resins (polyacrylic acid and derivatives thereof) such as polyacrylic acid salts and partially hydrolyzed polyacrylamides. Of these thickeners the preferred are natural water-soluble polymers, particularly alginic acid salts; cellulosic resins, particularly carboxymethyl cellulose salts; and acrylic resins, especially polyacrylic acid salts and partially hydrolyzed polyacrylamides.

Flowable formulations can be prepared by blending and grinding the above components. Flowable formulations are preferably produced by blending the active ingredients coarsely cracked to 150 micron or less, surfactants and aqueous solutions of water-soluble polymers, grinding the resultant mixture to a particle size of 5 micron or less by passing the material through a sand grinder, and then dispersing the material to form a suspension. Thereafter, the suspension is mixed with an aqueous solution of thickeners in a proper ratio.

The herbicidal composition of the present invention can be applied to waterfields, dry fields, orchards, lawns, pastures, tea-gardens, mulberry fields, forests, nonagricultural lands and the like.

The herbicidal composition of the present invention may be applied either before or after germination of weeds, and may be applied to leaves and stems or to land soils, or both. The application of herbicidal compositions can be carried out with conventional devices such as power dusters, boom and hand sprayers, spray dusters, spreaders, and the like. The herbicidal compositions may be applied either directly without dilution or may be diluted with water or other solvents such as alcohol.

The amount of the active ingredients needed to control weeds will vary according to the particular end results desired. For general herbicidal effects, herbicidal compositions are applied at a rate of usually 1-50 g or more, preferably 1-10 g of the active ingredients, per hectare.

Having generally described the invention, a more complete understanding can be obtained by reference to certain specific examples, which are included for purposes of illustration only and are not intended to be limiting unless otherwise specified.

EXAMPLE 1

This example describes the preparation of N-(alpha,alpha-dimethylbenzyl)-1,4-dihydro-alpha-naphthoamide [Compound No. I-11].

Into a 200 ml. round bottom flask equipped with a thermometer, a stirrer, a reflux condenser and a dropping funnel, were charged 80 ml. of ether, 3.03 g of triethyl amine and 4.05 g. of alpha,alpha-dimethylbenzylamine. Thereto, 5.78 g of 1,4-dihydro-alpha-naphthoic chloride were added dropwise with stirring at such a speed as to reflux ether gently. Thereafter, stirring was continued for 30 minutes.

To the resulting product, 50 ml. of water was added, followed by stirring for 10 minutes. Then, ether was removed by distillation and the residue was filtered to obtain a white solid. After recrystallization of the solid from a mixture of methanol and water, there was obtained 8.34 g (Yield 95.5%) of Compound No. I-11.

EXAMPLE 2

This example describes the preparation of 1,2,3,4-tetrahydro-alpha-naphthoic acid.

Into a 200 ml. beaker were charged 40 g. (1.74 mol.) of pieces of metallic sodium and 400 ml. (2.93 mol.) of tetralin, followed by melting the sodium under heating. Maintaining the temperature at 110° C., the mixture was stirred at 15000-18000 r.p.m. for 5 minutes with a high-speed mixer. After cooling without stirring to room temperature, there was obtained a gray dispersion of particulate metallic sodium distributed in tetralin. These manipulations were carried out in a dry box.

In a 1000 ml. three-necked flask equipped with a thermometer, a stirrer and a dropping funnel, 426.5 g. of the dispersion of particulate metallic sodium in tetralin were charged; and, while stirring with cooling in an ice bath, 85 g. (0.755 mol.) of chlorobenzene were added dropwise slowly at a temperature not exceeding 50° C., followed by continued stirring for an hour at room temperature for maturation.

Then, while stirring with cooling in an ice bath, 87.6 g. (0.755 mol.) of chlorobenzene were added dropwise slowly at temperatures not exceeding 40° C., followed by continued stirring for an hour at room temperature for maturation to obtain a dispersion of 1,2,3,4-tetrahydro-1-naphthyl sodium.

In a 3000 ml. four-necked flask equipped with a thermometer, a stirrer, a dropping funnel and a gas inlet tube, 500 ml. of diethyl ether were charged; and, while cooling in an ice bath, carbon dioxide gas was passed through and dissolved in the ether. Subsequently, while passing $CO_2$ gas, the dispersion of 1,2,3,4-tetrahydro-1- naphthyl sodium was added dropwise at a temperature not exceeding 40° C., followed by continued stirring for an hour while passing carbon dioxide gas.

To the resulting mixture, was added 800 ml. of 0.5N aqueous solution of sodium hydroxide. The mixture was stirred vigorously, and was then allowed to separate into an organic phase and an aqueous phase. Hydrochloric acid was added slowly to the aqueous phase to adjust the phase to a pH of 1-2, whereby a white precipitate formed. The precipitate was filtered with suction and dried to obtain 129 g. of crude 1,2,3,4-tetrahydro-1-naphthoic acid. The crude acid was recrystallized from a mixture of methanol and water to obtain 120 g. of colorless needles of 1,2,3,4-tetrahydro-1-naphthoic acid having the following properties:

Melting point: 83.5–84° C.
NMR spectrum: 2.0 ppm, 2.78 ppm, 3.77 ppm, 6.9–7.2 ppm, 11.7 ppm.

Elemental analysis:

|  | C | H | O |
|---|---|---|---|
| Observed, % | 74.8 | 6.9 | 18.3 |
| (Theoretical, % | 75.0 | 6.8 | 18.2) |

EXAMPLE 3

This example describes an alternative preparation of 1,2,3,4-tetrahydro-1-naphthoic acid.

By repeating the above procedure of Example 2 except that, instead of adding the dispersion of 1,2,3,4-tetrahydro-1-naphthyl sodium to the ether containing carbon dioxide gas dissolved therein, carbon dioxide gas was passed while the dispersion of 1,2,3,4-tetrahydro-1-naphthyl sodium diluted with 500 ml. of tetralin was stirred. 112 grams of colorless needles of 1,2,3,4-tetrahydro-1-naphthoic acid were obtained.

EXAMPLE 4

This example describes the preparation of N-(p-chloro-alpha-ethyl-alpha-methylbenzyl)-1,2,3,4-tetrahydro-alpha-naphthoamide [Compound No. III-22].

In a 200 ml. round bottom flask equipped with a thermometer, a stirrer and a reflux condenser, 2.64 g. of 1,2,3,4-tetrahydro-alpha-naphthoic acid, produced according to Example 2, were dissolved into 90 ml. of methylene chloride. To the mixture were added 2.75 g. of p-chloro-alpha-ethyl-alpha-methylbenzyl amine, 3.64 g. of triethyl amine and 4.59 g. of N-methyl-2-chloropyridinium iodide in order, followed by heating to reflux temperature for an hour and then cooling to room temperature.

To the resulting product, 30 ml. of 5% hydrochloric acid was added, followed by removal of the solvent by distillation under reduced pressure. The residue was filtered and dried, followed by recrystallization from a mixture of methanol and water to obtain 4.86 g. (Yield 94.7%) of Compound No. III-22.

EXAMPLE 5

Wettable powders were produced by blending and grinding 10 parts of Compound No. I-11, 55 parts of kaolin, 30 parts of bentonite and 5 parts of sodium lignin sulfonate.

EXAMPLE 6

Granules were produced by blending and grinding 10 parts of Compound No. III-22, 55 parts of bentonite, 32 parts of talc and 3 parts of sodium naphthalene sulfonate, followed by blending with a proper amount of water and then granulating the resultant blend with a granulator.

EXAMPLE 7

The example describes the herbicidal properties of compounds of the present invention.

The various weed seeds described below were uniformly mixed and sowed on the surface of waterfield soil (clay loam) charged in 1/5000 are pots. Subsequently, two- or three-leaved young seedlings of waterfield rice plants were transplanted at a depth of 2 cm, followed by filling of the pots with water to the brim. Then, at an early stage of development of the weeds after 3 days, fixed amounts of each compound of this invention were sprayed onto the filled water surface. Herbicidal effects were observed 3 weeks after spraying. The results are shown in Table 6.

Damage to plants was assessed on a scale of 0–5, as follows:

0: no damage; 1: slightly damaged; 2: damaged to a small extent; 3: damaged to a medium extent;
4: damaged severely and 5: perfectly killed.

The names of weeds tested are as follows:
Ec: *Echinochloa crus-galli;*
Bl: broad leaf weeds (*Rotala indica, Lindernia pyxidari*);
Sj: *Scirpus juncoides;*
Cd: *Cyperus difformis;* and
Mv: *Monochoria vaginaris*

TABLE 6

| Compound No. | Rate, g/are | Phytotoxity to rice | Herbicidal effects | | | | |
|---|---|---|---|---|---|---|---|
| | | | Ec | Bl | Sj | Cd | Mv |
| I-1 | 25 | 0 | 2 | 2 | 0 | 4 | 2 |
| | 12.5 | 0 | 1 | 0 | 0 | 2 | 0 |
| I-2 | 25 | 0 | 4 | 5 | 0 | 5 | 5 |
| | 12.5 | 0 | 3 | 5 | 0 | 4 | 3 |
| I-3 | 25 | 0 | 2 | 3 | 2 | 3 | 3 |
| | 12.5 | 0 | 1 | 1 | 1 | 2 | 2 |
| I-4 | 25 | 0 | 2 | 3 | 2 | 2 | 3 |
| | 12.5 | 0 | 0 | 0 | 1 | 0 | 0 |
| I-5 | 25 | 0 | 2 | 3 | 2 | 5 | 5 |
| | 12.5 | 0 | 1 | 1 | 0 | 2 | 4 |
| I-6 | 25 | 0 | 2 | 3 | 1 | 4 | 4 |
| | 12.5 | 0 | 0 | 0 | 0 | 1 | 1 |
| I-7 | 25 | 0 | 2 | 3 | 4 | 2 | 3 |
| | 12.5 | 0 | 0 | 1 | 2 | 0 | 2 |
| I-8 | 25 | 0 | 3 | 3 | 4 | 3 | 3 |
| | 12.5 | 0 | 2 | 1 | 3 | 2 | 3 |
| I-9 | 25 | 0 | 3 | 4 | 4 | 5 | 4 |
| | 12.5 | 0 | 2 | 3 | 3 | 5 | 3 |
| I-10 | 25 | 0 | 2 | 4 | 4 | 5 | 4 |
| | 12.5 | 0 | 1 | 2 | 2 | 4 | 2 |
| I-11 | 25 | 0 | 5 | 4 | 5 | 5 | 5 |
| | 12.5 | 0 | 5 | 2 | 5 | 5 | 5 |
| I-12 | 25 | 0 | 5 | 3 | 4 | 5 | 5 |
| | 12.5 | 0 | 4 | 2 | 2 | 3 | 4 |
| I-13 | 25 | 0 | 5 | 4 | 5 | 5 | 5 |
| | 12.5 | 0 | 5 | 2 | 5 | 5 | 5 |
| I-14 | 25 | 0 | 5 | 3 | 2 | 4 | 4 |
| | 12.5 | 0 | 4 | 2 | 0 | 3 | 2 |
| I-15 | 25 | 0 | 5 | 4 | 4 | 5 | 5 |
| | 12.5 | 0 | 5 | 3 | 2 | 5 | 5 |
| I-16 | 25 | 0 | 4 | 2 | 2 | 5 | 5 |
| | 12.5 | 0 | 2 | 0 | 0 | 5 | 5 |
| I-17 | 25 | 0 | 2 | 0 | 2 | 4 | 2 |
| | 12.5 | 0 | 0 | 0 | 0 | 2 | 0 |
| I-18 | 25 | 0 | 5 | 2 | 2 | 5 | 5 |
| | 12.5 | 0 | 5 | 0 | 0 | 5 | 4 |
| I-19 | 25 | 0 | 5 | 3 | 4 | 5 | 5 |
| | 12.5 | 0 | 5 | 2 | 2 | 4 | 3 |
| I-20 | 25 | 0 | 4 | 2 | 2 | 5 | 3 |
| | 12.5 | 0 | 2 | 0 | 0 | 4 | 2 |
| I-21 | 25 | 0 | 5 | 0 | 3 | 5 | 5 |

TABLE 6-continued

| Compound No. | Rate, g/are | Phytotoxicity to rice | Herbicidal effects |||||
|---|---|---|---|---|---|---|---|
| | | | Ec | Bl | Sj | Cd | Mv |
| | 12.5 | 0 | 5 | 0 | 3 | 5 | 5 |
| I-22 | 25 | 0 | 5 | 2 | 4 | 5 | 5 |
| | 12.5 | 0 | 5 | 2 | 4 | 5 | 5 |
| I-23 | 25 | 0 | 5 | 2 | 5 | 5 | 5 |
| | 12.5 | 0 | 5 | 0 | 4 | 5 | 5 |
| I-24 | 25 | 0 | 5 | 2 | 4 | 5 | 5 |
| | 12.5 | 0 | 5 | 0 | 3 | 4 | 4 |
| II-1 | 25 | 0 | 4 | 3 | 3 | 3 | 2 |
| | 12.5 | 0 | 2 | 2 | 2 | 2 | 1 |
| II-2 | 25 | 0 | 4 | 2 | 3 | 4 | 3 |
| | 12.5 | 0 | 3 | 1 | 1 | 2 | 2 |
| II-3 | 25 | 0 | 4 | 2 | 2 | 4 | 4 |
| | 12.5 | 0 | 3 | 1 | 1 | 3 | 4 |
| II-4 | 25 | 0 | 5 | 4 | 3 | 5 | 4 |
| | 12.5 | 0 | 5 | 2 | 2 | 4 | 3 |
| II-5 | 25 | 0 | 4 | 0 | 2 | 4 | 3 |
| | 12.5 | 0 | 2 | 0 | 0 | 2 | 2 |
| II-6 | 25 | 0 | 5 | 3 | 3 | 4 | 3 |
| | 12.5 | 0 | 4 | 2 | 2 | 3 | 3 |
| II-7 | 25 | 0 | 3 | 0 | 0 | 3 | 2 |
| | 12.5 | 0 | 2 | 0 | 0 | 2 | 0 |
| II-8 | 25 | 0 | 2 | 0 | 0 | 2 | 0 |
| | 12.5 | 0 | 0 | 0 | 0 | 0 | 0 |
| II-9 | 25 | 0 | 5 | 5 | 5 | 5 | 5 |
| | 12.5 | 0 | 5 | 4 | 5 | 5 | 5 |
| II-10 | 25 | 0 | 5 | 4 | 5 | 5 | 5 |
| | 12.5 | 0 | 5 | 3 | 4 | 5 | 5 |
| II-11 | 25 | 0 | 5 | 4 | 4 | 5 | 5 |
| | 12.5 | 0 | 5 | 3 | 3 | 5 | 5 |
| II-12 | 25 | 0 | 5 | 4 | 4 | 5 | 5 |
| | 12.5 | 0 | 5 | 3 | 2 | 5 | 5 |
| II-13 | 25 | 0 | 5 | 2 | 2 | 4 | 4 |
| | 12.5 | 0 | 5 | 1 | 0 | 3 | 2 |
| II-14 | 25 | 0 | 5 | 4 | 5 | 5 | 5 |
| | 12.5 | 0 | 5 | 3 | 4 | 5 | 5 |
| II-15 | 25 | 0 | 5 | 2 | 0 | 4 | 3 |
| | 12.5 | 0 | 4 | 0 | 0 | 3 | 2 |
| II-16 | 25 | 0 | 5 | 5 | 5 | 5 | 5 |
| | 12.5 | 0 | 5 | 3 | 4 | 5 | 5 |
| II-17 | 25 | 0 | 5 | 2 | 3 | 5 | 5 |
| | 12.5 | 0 | 4 | 0 | 2 | 5 | 4 |
| II-18 | 25 | 0 | 5 | 0 | 2 | 4 | 2 |
| | 12.5 | 0 | 3 | 0 | 0 | 2 | 0 |
| III-1 | 25 | 0 | 3 | 3 | 3 | 3 | 4 |
| | 12.5 | 0 | 3 | 2 | 2 | 3 | 3 |
| III-2 | 25 | 0 | 4 | 3 | 4 | 3 | 4 |
| | 12.5 | 0 | 3 | 1 | 2 | 1 | 4 |
| III-3 | 25 | 0 | 4 | 2 | 4 | 4 | 5 |
| | 12.5 | 0 | 4 | 0 | 4 | 3 | 4 |
| III-4 | 25 | 0 | 4 | 4 | 3 | 5 | 4 |
| | 12.5 | 0 | 3 | 2 | 2 | 4 | 3 |
| III-5 | 25 | 0 | 3 | 0 | 2 | 2 | 2 |
| | 12.5 | 0 | 2 | 0 | 0 | 0 | 0 |
| III-6 | 25 | 0 | 5 | 2 | 2 | 5 | 5 |
| | 12.5 | 0 | 3.5 | 0 | 0 | 4 | 3 |
| III-7 | 25 | 0 | 5 | 2 | 3 | 4 | 3 |
| | 12.5 | 0 | 4 | 1 | 2 | 4 | 3 |
| III-8 | 25 | 0 | 5 | 2 | 2 | 5 | 5 |
| | 12.5 | 0 | 3 | 0 | 0 | 3 | 4 |
| III-9 | 25 | 0 | 4 | 0 | 2 | 5 | 4 |
| | 12.5 | 0 | 2 | 0 | 0 | 2 | 2 |
| III-10 | 25 | 0 | 5 | 5 | 5 | 5 | 5 |
| | 12.5 | 0 | 5 | 5 | 5 | 5 | 5 |
| III-11 | 25 | 0 | 5 | 5 | 5 | 5 | 5 |
| | 12.5 | 0 | 5 | 4 | 5 | 5 | 5 |
| III-12 | 25 | 0 | 5 | 5 | 5 | 5 | 5 |
| | 12.5 | 0 | 5 | 5 | 5 | 5 | 5 |
| III-13 | 25 | 0 | 5 | 5 | 5 | 5 | 5 |
| | 12.5 | 0 | 5 | 4 | 5 | 5 | 5 |
| III-14 | 25 | 0 | 5 | 5 | 5 | 5 | 5 |
| | 12.5 | 0 | 5 | 4 | 5 | 5 | 4 |
| III-15 | 25 | 0 | 5 | 5 | 5 | 5 | 5 |
| | 12.5 | 0 | 5 | 4 | 4 | 5 | 5 |
| III-16 | 25 | 0 | 5 | 3 | 3 | 5 | 5 |
| | 12.5 | 0 | 4 | 2 | 2 | 5 | 4 |
| III-17 | 25 | 0 | 5 | 5 | 5 | 5 | 5 |
| | 12.5 | 0 | 5 | 4.5 | 5 | 5 | 5 |
| III-18 | 25 | 0 | 5 | 5 | 5 | 5 | 5 |
| | 12.5 | 0 | 5 | 4.5 | 5 | 5 | 5 |

TABLE 6-continued

| Compound No. | Rate, g/are | Phytotoxicity to rice | Herbicidal effects |||||
|---|---|---|---|---|---|---|---|
| | | | Ec | Bl | Sj | Cd | Mv |
| III-19 | 25 | 0 | 5 | 5 | 5 | 5 | 5 |
| | 12.5 | 0 | 5 | 3.5 | 3.5 | 5 | 5 |
| III-20 | 25 | 0 | 5 | 3 | 4 | 5 | 5 |
| | 12.5 | 0 | 3 | 2 | 3 | 5 | 4 |
| III-21 | 25 | 0 | 5 | 3 | 5 | 5 | 5 |
| | 12.5 | 0 | 5 | 2 | 5 | 5 | 4 |
| III-22 | 25 | 0 | 5 | 2 | 5 | 5 | 5 |
| | 12.5 | 0 | 5 | 0 | 4 | 4 | 4 |

EXAMPLE 8

This example describes the herbicidal properties of wettable powders of the invention.

Example 7 was repeated except that forced germination seeds of waterfield rice plants described below were sowed, instead of transplanting two- or three-leaved young seedling of waterfield rice plants; and that wettable powders diluted with water were used as herbicides. The results are shown in Table 7. The names of weeds tested are as follows:

AK: Akibare, made in Japan; Nb: New Bonnet, made in U.S.A.; IR: IR-8, made in Philippine.

TABLE 7

| Compound No. | Rate, g/are | Phytotoxicity to rice ||| Herbicidal effects |||||
|---|---|---|---|---|---|---|---|---|---|
| | | AK | Nb | IR | Ec | Bl | Mv | Cd | Sj |
| I-11 | 200 | 0 | 0 | 0 | 5 | 4 | 5 | 5 | 5 |
| | 100 | 0 | 0 | 0 | 5 | 2 | 5 | 5 | 5 |
| | 50 | 0 | 0 | 0 | 4 | 0 | 4 | 2 | 3 |
| III-10 | 200 | 0 | 0 | 0 | 5 | 5 | 5 | 5 | 5 |
| | 100 | 0 | 0 | 0 | 5 | 5 | 5 | 5 | 5 |
| | 50 | 0 | 0 | 0 | 5 | 4 | 4.5 | 5 | 5 |
| Blank | 0 | 0 | 0 | 0 | 0 | 0 | 0 | 0 | 0 |

EXAMPLE 9

This example describes the herbicidal properties of granules of the invention, tested in a waterfield.

The field was tilled and puddled by a conventional method, and young seedlings of waterfield rice plants were transplanted with the use of a rice-planting machine. The rice field was divided with corrugated sheet-zinc into lots of ground having 1 m² area; and granules were applied by hand at the germination stage of Echinochloa crus-galli 3 days after rice-planting and also at the two- or three-leaved stage of the weed 15 days after rice-planting. Herbicidal effects and phytotoxicity to rice were observed for 20 days after application. The results are shown in Table 8.

The names of weeds tested are as follows:

Ec: *Echinochloa crus-galli;*

Bl: broad leaf weeds (*Rotala indica, Lindernia pyxidari*);

Mv: *Monochoria vaginaris;*

Cs: *Cyperus serotinus;* and

Ek: *Eleocharis kuroguwai*

Compound No. X in Table 8 is S-(4-chlorobenzyl)-N,N-diethylthiolcarbamate, for comparison.

TABLE 8

| Compound No. | Rate, g/are | Phytotoxicity to rice | Herbicidal effects |||||
|---|---|---|---|---|---|---|---|
| | | | Ec | Bl | Mv | Cs | Ek |
| I-11 | 25 | 0 | 5 | 3 | 5 | 5 | 5 |
| | 12.5 | 0 | 3 | 2 | 3 | 4 | 4 |
| | 6.25 | 0 | 2 | 0 | 2 | 3 | 3 |
| I-13 | 25 | 0 | 5 | 4 | 5 | 5 | 5 |

TABLE 8-continued

| Compound No. | Rate, g/are | Phytotoxity to rice | Herbicidal effects | | | | |
|---|---|---|---|---|---|---|---|
| | | | Ec | Bl | Mv | Cs | Ek |
| | 12.5 | 0 | 5 | 2 | 5 | 5 | 5 |
| | 6.25 | 0 | 5 | 0 | 5 | 4 | 3 |
| I-18 | 25 | 0 | 5 | 2 | 5 | 5 | 5 |
| | 12.5 | 0 | 5 | 0 | 4 | 4 | 4 |
| | 6.25 | 0 | 5 | 0 | 3 | 3 | 2 |
| II-9 | 25 | 0 | 5 | 5 | 5 | 5 | 5 |
| | 12.5 | 0 | 5 | 4 | 5 | 4 | 4 |
| | 6.25 | 0 | 5 | 2 | 4.5 | 3 | 2 |
| II-10 | 25 | 0 | 5 | 4 | 5 | 5 | 5 |
| | 12.5 | 0 | 5 | 3 | 5 | 4 | 4 |
| | 6.25 | 0 | 4 | 2 | 3 | 3 | 2 |
| II-12 | 25 | 0 | 5 | 4 | 5 | 5 | 5 |
| | 12.5 | 0 | 4 | 3 | 5 | 4 | 4 |
| | 6.25 | 0 | 3 | 3 | 4 | 3 | 2 |
| III-10 | 25 | 0 | 5 | 5 | 5 | 5 | 5 |
| | 12.5 | 0 | 5 | 4 | 5 | 5 | 5 |
| | 6.25 | 0 | 5 | 3 | 5 | 4.5 | 4 |
| III-12 | 25 | 0 | 5 | 4 | 5 | 5 | 5 |
| | 12.5 | 0 | 5 | 3 | 5 | 5 | 5 |
| | 6.25 | 0 | 5 | 2 | 5 | 4.5 | 4 |
| III-19 | 25 | 0 | 5 | 5 | 5 | 5 | 5 |
| | 12.5 | 0 | 5 | 4 | 5 | 5 | 5 |
| | 6.25 | 0 | 5 | 3 | 5 | 4.5 | 4 |
| X | 25 | 0 | 5 | 5 | 4 | 5 | 4.5 |
| | 12.5 | 0 | 5 | 4 | 3 | 4 | 3 |
| | 6.25 | 0 | 4 | 3 | 2 | 2 | 2 |
| Blank | 0 | 0 | 0 | 0 | 0 | 0 | 0 |

EXAMPLE 10

This example describes the herbicidal properties of wettable powders under land field conditions.

Soil containing various weed seeds and tubers of Cyperus rotundus charged in unglazed pots was sowed with seed corn and soy beans to a depth of 2 cm, followed by leveling the soil surface. Then, a wettable powder diluted with water was applied without delay on the soil surface. Herbicidal effects and phytotoxity of crops were observed 4 weeks after application. The results are shown in Table 9.

The names of weeds tested are as follows:
Da: *Digitaria adscendens;*
Av: *Amaranthus viridis;*
Ps: *Polygonum sp.;*
Ca: *Chenopodium album* L.; and
Cr: *Cyperus rotundus*

Compound No. XI in Table 9 is 2-chloro-4,6-bis(ethylamino)-s-triazine, for comparison.

| Compound No. | Rate, g/are | Phytotoxity | | Herbicidal effects | | | | |
|---|---|---|---|---|---|---|---|---|
| | | Corn | Soybean | Da | Av | Ps | Ca | Cr |
| I-15 | 25 | 0 | 0 | 5 | 4 | 4 | 4 | 5 |
| | 12.5 | 0 | 0 | 5 | 3 | 3 | 3 | 5 |
| | 6.25 | 0 | 0 | 5 | 2 | 2 | 2 | 4 |
| II-9 | 25 | 0 | 0 | 5 | 4 | 4 | 4 | 5 |
| | 12.5 | 0 | 0 | 5 | 3 | 3.5 | 3 | 5 |
| | 6.25 | 0 | 0 | 5 | 2 | 3 | 2 | 4 |
| III-10 | 25 | 0 | 0 | 5 | 4 | 4 | 4.5 | 5 |
| | 12.5 | 0 | 0 | 5 | 3 | 3 | 4 | 5 |
| | 6.25 | 0 | 0 | 5 | 3 | 2 | 3 | 5 |
| III-12 | 25 | 0 | 0 | 5 | 4 | 4 | 4.5 | 5 |
| | 12.5 | 0 | 5 | 5 | 3.5 | 3 | 3.5 | 5 |
| | 6.25 | 0 | 0 | 5 | 3 | 2 | 2 | 5 |
| XI | 25 | 0 | 1.5 | 5 | 5 | 5 | 5 | 0 |
| | 12.5 | 0 | 0 | 5 | 5 | 4 | 4 | 0 |
| Blank | 0 | 0 | 0 | 0 | 0 | 0 | 0 | 0 |

EXAMPLE 11

This example describes the herbicidal properties of wettable powders applied to the stem and leaves under land field conditions.

Soil containing various weed seeds charged in unglazed pots was sowed with seed corn, wheat and soy beans to a depth of 2 cm. Thereafter, at the three- or four-leaved stage of these crops, emulsifiable concentrates diluted with water were applied over all the surface. Herbicidal effects and phytotoxity upon crops were observed 15 days after application. The results are shown in Table 10.

The names of weeds tested are as follows:
Da: *Digitaria adscendens;*
Pn: *Polygonum nodosum;*
Ca: *Chenopodium album* L.; and
Ci: *Cyperus iria.*

Compound No. XII in Table 10 is 3,4-dichloropropionanilide, for comparison.

TABLE 10

| Compound No. | Rate, g/are | Phytotoxity | | | Herbicidal effects | | | |
|---|---|---|---|---|---|---|---|---|
| | | Corn | Wheat | Soybean | Da | Pn | Ca | Ci |
| I-11 | 25 | 0 | 0 | 0 | 5 | 3 | 2 | 4 |
| | 12.5 | 0 | 0 | 0 | 4 | 2 | 0 | 3 |
| | 6.25 | 0 | 0 | 0 | 3 | 0 | 0 | 2 |
| III-10 | 25 | 0 | 0 | 0 | 5 | 5 | 4 | 4.5 |
| | 12.5 | 0 | 0 | 0 | 5 | 2 | 2 | 4 |
| | 6.25 | 0 | 0 | 0 | 4 | 0 | 0 | 3 |
| III-12 | 25 | 0 | 0 | 0 | 5 | 5 | 4 | 5 |
| | 12.5 | 0 | 0 | 0 | 5 | 3 | 3 | 5 |
| | 6.25 | 0 | 0 | 0 | 4.5 | 2 | 2 | 4 |
| XII | 25 | 5 | 3.5 | 5 | 5 | 5 | 5 | 5 |
| | 12.5 | 4 | 2 | 5 | 5 | 5 | 5 | 4 |
| | 6.25 | 3 | 1 | 4 | 4 | 4 | 4 | 3 |
| Blank | 0 | 0 | 0 | 0 | 0 | 0 | 0 | 0 |

EXAMPLE 12

Example 7 was repeated except that the following herbicidal formulations were used.

(a) G1 to G5:

Granulates produced by blending the ingredients listed in Table 11, adding a proper amount of water and kneading sufficiently with a kneader, followed by extrusion granulation through a screen of 0.7 mm diameter and then drying to obtain granulates of 1 mm length.

TABLE 11

| | Granule Formulations | | | | |
|---|---|---|---|---|---|
| Formulation No. | G1 | G2 | G3 | G4 | G5 |
| Compound No. III-10 | 3 | — | — | — | — |
| Compound No. I-11 | — | 3 | — | — | — |
| Compound No. I-9 | — | — | 3 | — | — |
| Compound No. I-11 | — | — | — | 3 | — |
| Compound No. I-23 | — | — | — | — | 3 |
| Sodium dioctylsulfosuccinate | 3 | — | 3 | 3 | 3 |
| Nonipol 100* | 2 | — | 2 | 2 | 2 |
| Sodium ligninsulfonate | — | 5 | — | — | — |
| Polyvinyl alcohol | — | 1 | — | — | — |
| Bentonite | 30 | — | 30 | 30 | 30 |
| Clay | 62 | — | 62 | 62 | 62 |
| Calcium carbonate | — | 91 | — | — | — |

Note
*Polyoxyethylene nonylphenylether, produced by Sanyo Chemical Industries, Ltd.

(b) W1 to W4:

Wettable powders produced by crushing a blend of the herbicide and the carrier described in Table 12, and further pulverizing to particle size of 2 micron with a jet mill (W1, 3 and 4) or micron mill (W2), followed by adding the surfactant described in Table 12 to the resulting finely divided powders in a ribbon mixer and then uniformly blending to form wettable powders.

TABLE 12

| Formulation No. | W1 | W2 | W3 | W4 |
|---|---|---|---|---|
| Herbicide | | | | |
| Compound No. II-9 | 50 | — | — | — |
| Compound No. I-9 | — | 50 | — | — |
| Compound No. III-10 | — | — | 50 | — |
| Compound No. III-15 | — | — | — | 50 |
| Carrier | | | | |
| Clay | 45 | — | — | — |
| Kaolin | — | 43 | — | — |
| Diatomaceous earth | — | — | 45 | 45 |
| Surfacants | | | | |
| Sodium MN sulfonate* | 5 | — | — | — |
| Sodium ligninsulfonate | — | 5 | — | — |
| Nonipol 80** | — | 2 | — | — |
| Sodium POE NP sulfate*** | — | — | 5 | 5 |

Notes
*Sodium methylnaphthalenesulfonate
**Polyoxyethylene nonylphenylether, produced by Sanyo Chemical Industries, Ltd.
***sodium polyoxyethylenenonylphenyl ether sulfate (c) F1 to F13:

Flowable formulations produced by blending the ingredients listed in Table 3, crushing to a particle size of less than 150 micron, and further pulverizing with a sand grinder of 500 ml vessel volume packed with 150 parts of Ottawa sand of particle size of about 1 mm, followed by adding 50 parts of 2% aqueous solution of carboxymethylcellulose sodium salt and blending flowable formulations.

TABLE 13

| | Flowable Formulations | | | |
|---|---|---|---|---|
| Formulation No. | F1 | F2 | F3 | F4 |
| Compound No. III-1 | 20 | — | — | — |
| Compound No. I-11 | — | 20 | — | — |
| Compound No. II-9 | — | — | 20 | — |
| Compound No. II-14 | — | — | — | 20 |
| Sorbitane trioleate | 1.5 | — | 1.5 | 1.5 |
| Nonipol 100* | — | 10 | — | — |
| Aqueous solution containing 2 parts of Polyvinyl alcohol | 28.5 | 20 | 28.5 | 28.5 |

Note
*Polyoxyethylene nonylphenylether, produced by Sanyo Chemical Industries, Ltd.

The results are shown in Table 14.

| Formulation No. | Rate, g/are | Phytotoxity to rice | Herbicidal effects | | | | |
|---|---|---|---|---|---|---|---|
| | | | Ec | Bl | Sj | Cd | Mv |
| G1 | 25 | 0 | 5 | 5 | 5 | 5 | 5 |
| | 12.5 | 0 | 5 | 4 | 5 | 5 | 5 |
| G2 | 25 | 0 | 5 | 4 | 5 | 5 | 5 |
| | 12.5 | 0 | 5 | 2 | 5 | 5 | 5 |
| G3 | 25 | 0 | 3 | 4 | 4 | 5 | 4 |
| | 12.5 | 0 | 2 | 3 | 3 | 5 | 3 |
| G4 | 25 | 0 | 5 | 4 | 5 | 5 | 5 |
| | 12.5 | 0 | 5 | 2 | 5 | 5 | 5 |
| G5 | 25 | 0 | 5 | 2 | 5 | 5 | 5 |
| | 12.5 | 0 | 5 | 0 | 4 | 5 | 5 |
| W1 | 25 | 0 | 5 | 5 | 5 | 5 | 5 |
| | 12.5 | 0 | 5 | 4 | 5 | 5 | 5 |
| W2 | 25 | 0 | 3 | 4 | 4 | 5 | 4 |
| | 12.5 | 0 | 2 | 3 | 3 | 5 | 3 |
| W3 | 25 | 0 | 5 | 5 | 5 | 5 | 5 |
| | 12.5 | 0 | 5 | 5 | 5 | 5 | 5 |
| W4 | 25 | 0 | 5 | 5 | 5 | 5 | 5 |
| | 12.5 | 0 | 5 | 4 | 4 | 5 | 5 |
| F1 | 25 | 0 | 5 | 5 | 5 | 5 | 5 |
| | 12.5 | 0 | 5 | 5 | 5 | 5 | 4 |
| F2 | 25 | 0 | 5 | 5 | 5 | 5 | 5 |
| | 12.5 | 0 | 5 | 5 | 5 | 5 | 5 |
| F3 | 25 | 0 | 5 | 5 | 5 | 5 | 5 |
| | 12.5 | 0 | 5 | 4 | 5 | 3 | 5 |
| F4 | 25 | 0 | 5 | 2 | 0 | 4.5 | 4.5 |
| | 12.5 | 0 | 5 | 0 | 0 | 4 | 4 |

EXAMPLE 13

Example 9 was repeated except that the above-mentioned herbicidal formulation G1, W3 and F3 were used.

The results are shown in Table 15.

TABLE 15

| Formulation No. | Rate, g/are | Phytotoxity to rice | Herbicidal effects | | | | |
|---|---|---|---|---|---|---|---|
| | | | Ec | Bl | Mv | Cs | Ek |
| G1 | 25 | 0 | 5 | 3 | 5 | 5 | 5 |
| | 12.5 | 0 | 3 | 2 | 3 | 4 | 4 |
| | 6.25 | 0 | 2 | 0 | 2 | 3 | 3 |
| W3 | 25 | 0 | 5 | 5 | 5 | 5 | 5 |
| | 12.5 | 0 | 5 | 4 | 5 | 5 | 5 |
| | 6.25 | 0 | 5 | 3 | 5 | 4.5 | 4 |
| F3 | 25 | 0 | 5 | 5 | 5 | 5 | 5 |
| | 12.5 | 0 | 5 | 4 | 5 | 4 | 4 |
| | 6.25 | 0 | 5 | 2 | 4.5 | 3 | 2 |
| X* | 25 | 0 | 5 | 5 | 4 | 5 | 4.5 |
| | 12.5 | 0 | 5 | 4 | 3 | 4 | 3 |
| | 6.25 | 0 | 4 | 3 | 2 | 2 | 2 |
| Blank | 0 | 0 | 0 | 0 | 0 | 0 | 0 |

Note
*the same as in Table 8.

EXAMPLE 14

Example 10 was repeated except that the above-mentioned herbicidal formulations W3 and F3 were used.

The results are shown in Table 16.

TABLE 16

| Formulation No. | Rate, g/are | Phytotoxity | | Herbicidal effects | | | | |
|---|---|---|---|---|---|---|---|---|
| | | Corn | Soybean | Da | Av | Ps | Ca | Cr |
| W3 | 25 | 0 | 0 | 5 | 4 | 4 | 4.5 | 5 |
| | 12.5 | 0 | 0 | 5 | 3 | 3 | 4 | 5 |
| | 6.25 | 0 | 0 | 5 | 3 | 2 | 3 | 5 |
| F3 | 25 | 0 | 0 | 5 | 4 | 4 | 4 | 5 |
| | 12.5 | 0 | 0 | 5 | 3 | 3.5 | 3 | 5 |
| | 6.25 | 0 | 0 | 5 | 2 | 3 | 2 | 4 |
| XI* | 25 | 0 | 1.5 | 5 | 5 | 5 | 5 | 0 |
| | 12.5 | 0 | 0 | 5 | 5 | 4 | 4 | 0 |
| Blank | 0 | 0 | 0 | 0 | 0 | 0 | 0 | 0 |

Note
*the same as in Table 9.

EXAMPLE 15

Example 11 was repeated except that the above-mentioned herbicidal formulations F1 and F2 were used.

The results are shown in Table 17.

| Compound No. | Rate, g/are | Phytotoxity | | | Herbicidal effects | | | |
|---|---|---|---|---|---|---|---|---|
| | | Corn | Wheat | Soybean | Da | Pn | Ca | Ci |
| F1 | 25 | 0 | 0 | 0 | 5 | 5 | 4 | 4.5 |
| | 12.5 | 0 | 0 | 0 | 5 | 2 | 2 | 4 |
| | 6.25 | 0 | 0 | 0 | 4 | 0 | 0 | 3 |
| F2 | 25 | 0 | 0 | 0 | 5 | 3 | 2 | 4 |
| | 12.5 | 0 | 0 | 0 | 4 | 2 | 0 | 3 |
| | 6.25 | 0 | 0 | 0 | 3 | 0 | 0 | 2 |
| XII | 25 | 5 | 3.5 | 5 | 5 | 5 | 5 | 5 |
| | 12.5 | 4 | 2 | 5 | 5 | 5 | 5 | 4 |
| | 6.25 | 3 | 1 | 4 | 4 | 4 | 4 | 3 |

-continued

| Compound No. | Rate, g/are | Phytotoxicity | | | Herbicidal effects | | | |
|---|---|---|---|---|---|---|---|---|
| | | Corn | Wheat | Soybean | Da | Pn | Ca | Ci |
| Blank | 0 | 0 | 0 | 0 | 0 | 0 | 0 | 0 |

Note
*the same as in Table 10.

EXAMPLE 16

Example 12(a) was repeated except that the following ingredients were used:

| | parts |
|---|---|
| Compound No. I-2 | 5 |
| Herbicide (w-1) | 7.5 |
| Toxanon GR-31A* | 4 |
| Bentonite | 53.5 |
| Talc | 30 |

Note
*polyacrylic salts, produced by Sanyo Chemical Industries

EXAMPLE 17

Example 7 was repeated except that granulates prepared from the active ingredients described in Table 18 by the same manner as described in Example 15 were used instead of wettable powders. The results are shown in Table 18.

TABLE 18

| Active ingredients | Rate, g/are | Phytotoxicity to rice | Herbicidal effects | | | | |
|---|---|---|---|---|---|---|---|
| | | | Ec | Bl | Sj | Cd | Mv |
| I-2 | 25 | 0 | 4 | 5 | 5 | 5 | 0 |
| | 12.5 | 0 | 3 | 5 | 3 | 4 | 0 |
| I-2 + Q-3 | 10 + 15 | 0 | 5 | 5 | 5 | 5 | 5 |
| | 5 + 7.5 | 0 | 4 | 5 | 3 | 5 | 5 |
| Q-3 | 25 | 0 | 5 | 5 | 5 | 5 | 5 |
| | 12.5 | 0 | 4 | 5 | 3 | 5 | 5 |
| I-23 | 25 | 0 | 5 | 2 | 5 | 5 | 5 |
| | 12.5 | 0 | 5 | 0 | 5 | 5 | 4 |
| I-23 + U-2 | 10 + 15 | 0 | 5 | 3 | 5 | 5 | 5 |
| | 5 + 7.5 | 0 | 5 | 2 | 5 | 5 | 4 |
| U-2 | 25 | 0 | 4 | 3 | 5 | 5 | 5 |
| | 12.5 | 0 | 3 | 2 | 4 | 4 | 4 |
| II-11 | 25 | 0 | 5 | 4 | 5 | 5 | 4 |
| | 12.5 | 0 | 5 | 3 | 5 | 5 | 3 |
| II-11 + N-3 | 10 + 15 | 0 | 5 | 5 | 5 | 5 | 5 |
| | 5 + 7.5 | 0 | 5 | 5 | 5 | 5 | 3 |
| N-3 | 25 | 0 | 4 | 5 | 5 | 5 | 4 |
| | 12.5 | 0 | 3 | 5 | 5 | 5 | 3 |
| II-17 | 25 | 0 | 5 | 2 | 5 | 5 | 3 |
| | 12.5 | 0 | 5 | 0 | 5 | 5 | 4 |
| II-17 + T-1 | 10 + 15 | 0 | 5 | 5 | 5 | 5 | 5 |
| | 5 + 7.5 | 0 | 5 | 4 | 4 | 5 | 5 |
| T-1 | 25 | 0 | 5 | 5 | 5 | 5 | 5 |
| | 12.5 | 0 | 5 | 4 | 3 | 5 | 5 |
| III-10 | 25 | 0 | 5 | 5 | 5 | 5 | 5 |
| | 12.5 | 0 | 5 | 5 | 5 | 5 | 5 |
| III-10 + U-1 | 10 + 15 | 0 | 5 | 5 | 5 | 5 | 5 |
| | 5 + 7.5 | 0 | 5 | 5 | 5 | 5 | 5 |
| U-1 | 25 | 0 | 5 | 4 | 5 | 5 | 5 |
| | 12.5 | 0 | 4 | 3 | 5 | 5 | 4 |
| III-15 | 25 | 0 | 5 | 5 | 5 | 5 | 5 |
| | 12.5 | 0 | 5 | 4 | 5 | 5 | 4 |
| III-15 + W-1 | 10 + 15 | 0 | 5 | 5 | 5 | 5 | 5 |
| | 5 + 7.5 | 0 | 5 | 5 | 5 | 5 | 5 |
| W-1 | 25 | 0 | 5 | 5 | 5 | 5 | 5 |
| | 12.5 | 0 | 4 | 5 | 4 | 5 | 5 |

EXAMPLE 18

Example 8 was repeated except that granulates prepared from the active ingredients described in Table 19 by the same manner as in Example 15 were used. The results are shown in Table 19.

| Active ingredients | Rate, g/are | Phytotoxicity to rice | | | Herbicidal effects | | | | |
|---|---|---|---|---|---|---|---|---|---|
| | | Ak | Nb | lR | Ec | Bl | Mv | Cd | Sj |
| I-2 | 20 | 0 | 0 | 0 | 4 | 5 | 5 | 5 | 0 |
| | 10 | 0 | 0 | 0 | 3 | 5 | 3 | 4 | 0 |
| | 5 | 0 | 0 | 0 | 3 | 5 | 3 | 4 | 0 |
| I-2 +U-1 | 14 + 6 | 0 | 0 | 0 | 5 | 5 | 5 | 5 | 5 |
| | 7 + 3 | 0 | 0 | 0 | 5 | 4 | 5 | 5 | 5 |
| | 3.5 + 1.5 | 0 | 0 | 0 | 4 | 2 | 4 | 3 | 4 |
| U-1 | 20 | 4 | 3 | 3 | 5 | 5 | 3 | 5 | 4 |
| | 10 | 2 | 1 | 1 | 5 | 4 | 2 | 5 | 2 |
| | 5 | 1 | 1 | 1 | 5 | 3 | 2 | 4 | 2 |
| I-2 +W-1 | 10 + 10 | 0 | 0 | 0 | 5 | 5 | 5 | 5 | 5 |
| | 5 + 5 | 0 | 0 | 0 | 5 | 5 | 5 | 5 | 5 |
| | 2.5 + 2.5 | 0 | 0 | 0 | 5 | 4 | 3 | 4 | 5 |
| W-1 | 20 | 2 | 2 | 2 | 5 | 5 | 5 | 5 | 5 |
| | 10 | 0 | 1 | 1 | 4 | 5 | 5 | 5 | 5 |
| | 5 | 0 | 0 | 0 | 2 | 4 | 4 | 4 | 4 |
| II-11 | 20 | 0 | 0 | 0 | 5 | 4 | 5 | 5 | 4 |
| | 10 | 0 | 0 | 0 | 5 | 3 | 5 | 5 | 3 |
| | 5 | 0 | 0 | 0 | 5 | 3 | 5 | 5 | 3 |
| II-11 + N-3 | 14 + 6 | 0 | 0 | 0 | 5 | 5 | 5 | 5 | 5 |
| | 7 + 3 | 0 | 0 | 0 | 5 | 5 | 5 | 5 | 5 |
| | 3.5 + 1.5 | 0 | 0 | 0 | 4 | 5 | 5 | 5 | 4 |
| N-3 | 20 | 3 | 3 | 3 | 4 | 5 | 5 | 5 | 4 |
| | 10 | 3 | 3 | 2 | 3 | 5 | 5 | 5 | 3 |
| | 5 | 2 | 3 | 1 | 3 | 4 | 4 | 4 | 3 |
| II-17 | 20 | 0 | 0 | 0 | 5 | 2 | 5 | 5 | 3 |
| | 10 | 0 | 0 | 0 | 4 | 0 | 4 | 5 | 2 |
| | 5 | 0 | 0 | 0 | 4 | 0 | 4 | 5 | 2 |
| II-17 +Q-3 | 16 + 4 | 0 | 0 | 0 | 5 | 5 | 5 | 5 | 5 |
| | 8 + 2 | 0 | 0 | 0 | 5 | 4 | 5 | 5 | 4 |
| | 4 + 1 | 0 | 0 | 0 | 5 | 3 | 5 | 5 | 4 |
| Q-3 | 20 | 5 | 5 | 5 | 5 | 5 | 5 | 5 | 5 |
| | 10 | 5 | 5 | 5 | 4 | 5 | 3 | 5 | 5 |
| | 5 | 4 | 4 | 5 | 4 | 4 | 2 | 4 | 4 |
| III-10 | 20 | 0 | 0 | 0 | 5 | 5 | 5 | 5 | 5 |
| | 10 | 0 | 0 | 0 | 5 | 5 | 5 | 5 | 5 |
| | 5 | 0 | 0 | 0 | 5 | 4 | 4.5 | 5 | 5 |
| III-10 + U-1 | 14 + 6 | 0 | 0 | 0 | 5 | 5 | 5 | 5 | 5 |
| | 7 + 3 | 0 | 0 | 0 | 5 | 5 | 5 | 5 | 5 |
| | 3.5 + 1.5 | 0 | 0 | 0 | 4 | 3 | 4 | 5 | 4 |
| III-10 +W-1 | 10 + 10 | 0 | 0 | 0 | 5 | 5 | 5 | 5 | 5 |
| | 5 + 5 | 0 | 0 | 0 | 5 | 5 | 5 | 5 | 5 |
| | 3.5 + 1.5 | 0 | 0 | 0 | 5 | 4 | 4 | 5 | 5 |
| III-15 | 20 | 0 | 0 | 0 | 5 | 5 | 5 | 5 | 5 |
| | 10 | 0 | 0 | 0 | 5 | 4 | 5 | 5 | 4 |
| | 5 | 0 | 0 | 0 | 5 | 4 | 5 | 5 | 4 |
| III-15 +T-1 | 16 + 4 | 0 | 0 | 0 | 5 | 5 | 5 | 5 | 5 |
| | 8 + 2 | 0 | 0 | 0 | 5 | 5 | 5 | 5 | 5 |
| | 4 + 1 | 0 | 0 | 0 | 5 | 4 | 4 | 5 | 5 |
| T-1 | 20 | 5 | 5 | 5 | 5 | 5 | 5 | 5 | 5 |
| | 10 | 5 | 4 | 4 | 5 | 4 | 3 | 5 | 5 |
| | 5 | 5 | 4 | 4 | 4 | 3 | 2 | 4 | 3 |
| Blank | 0 | 0 | 0 | 0 | 0 | 0 | 0 | 0 | 0 |

Having now fully described this invention, it will be apparent to one of ordinary skill in the art that many changes and modifications can be made thereto without departing from the spirit or scope of the invention as set forth herein.

What is claimed as new and desired to be secured by Letters Patent is:

1. A compound of the formula:

(1)

wherein R is 1,2,3,4-tetrahydro-1-naphthyl, 1,4-dihydro-1-naphthyl or 3,4-dihydro-1-naphthyl; $R_1$ is methyl; $R_2$ is methyl or ethyl; Ar is a phenylene group; and X is hydrogen, a halogen, methyl or methoxy.

2. The compound of claim 1, wherein X is fluorine, chlorine or bromine.

3. The compound of claim 1, wherein $R_2$ is methyl.

4. The compound of claim 1, wherein R is 1,2,3,4-tetrahydro-1-naphthyl.

5. The compound of claim 4, wherein
 (i) $R_1$ is methyl, $R_2$ is methyl and X is hydrogen, fluorine, chlorine, bromine, methyl or methoxy; or
 (ii) $R_1$ is methyl, $R_2$ is ethyl and X is hydrogen or chlorine.

6. The compound of claim 1, wherein R is 1,4-dihydro-1-naphthyl.

7. The compound of claim 6, wherein
 (i) $R_1$ is methyl, $R_2$ is methyl and X is hydrogen, fluorine, chlorine, bromine, methyl or methoxy; or
 (ii) $R_1$ is methyl, $R_2$ is ethyl and X is hydrogen or chlorine.

8. The compound of claim 1, wherein R is 3,4-dihydro-1-naphthyl.

9. The compound of claim 8, wherein
 $R_1$ is methyl, $R_2$ is methyl and X is hydrogen, fluorine, chlorine, bromine, methyl or methoxy.

10. A herbicidal composition, which comprises a herbicidally effective amount of at least one herbicide comprising a compound of the formula:

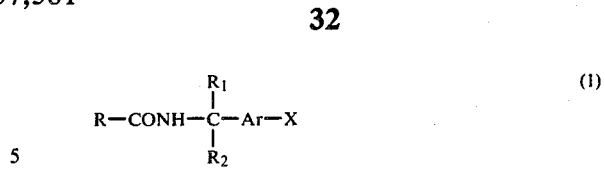

wherein R is 1,2,3,4-tetrahydro-1-naphthyl, 1,4-dihydro-1-naphthyl or 3,4-dihydro-1-naphthyl; $R_1$ is methyl; $R_2$ is methyl or ethyl; Ar is a phenylene group; and X is hydrogen, a halogen, methyl or methoxy; in admixture with at least one agricultural adjuvant selected from the group consisting of surfactants, water-soluble polymers and carriers.

11. The composition of claim 10, which further comprises at least one herbicide selected from the group consisting of phenoxy-type, diphenylether-type, amide-type, carbamate-type, diazole-type, pyrazole-type, urea-type and triazine-type herbicides.

12. The composition of claim 10 or 11, which comprises
 0.5–90% of said herbicide;
 0.1–20% of a surfactant or a water-soluble polymer, or both; and
 0.99% of a carrier, based on the total weight of the composition.

13. The composition of claim 12, in the form of a dust, a wettable powder, granules, a concentrate or a suspension.

* * * * *